US009796765B2

(12) United States Patent
Sato et al.

(10) Patent No.: US 9,796,765 B2
(45) Date of Patent: Oct. 24, 2017

(54) MODIFIED LECTIN DERIVED FROM WISTERIA FLORIBUNDA

(71) Applicant: NATIONAL INSTITUTE OF ADVANCED INDUSTRIAL SCIENCE AND TECHNOLOGY, Tokyo (JP)

(72) Inventors: Takashi Sato, Tsukuba (JP); Yasunori Chiba, Tsukuba (JP); Hiroaki Tateno, Tsukuba (JP); Hiroyuki Kaji, Tsukuba (JP); Masanori Goto, Tsukuba (JP); Hisashi Narimatsu, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/654,223

(22) PCT Filed: Dec. 18, 2013

(86) PCT No.: PCT/JP2013/083854
§ 371 (c)(1),
(2) Date: Jun. 19, 2015

(87) PCT Pub. No.: WO2014/098112
PCT Pub. Date: Jun. 26, 2014

(65) Prior Publication Data
US 2015/0329602 A1    Nov. 19, 2015

(30) Foreign Application Priority Data
Dec. 21, 2012 (JP) ................. 2012-280092

(51) Int. Cl.
*C07K 14/42*    (2006.01)
*G01N 33/53*    (2006.01)

(52) U.S. Cl.
CPC ......... *C07K 14/42* (2013.01); *G01N 33/5308* (2013.01); *G01N 2333/42* (2013.01); *G01N 2400/00* (2013.01)

(58) Field of Classification Search
CPC .......................... C07K 14/42; G01N 33/5308
See application file for complete search history.

(56) References Cited

U.S. PATENT DOCUMENTS

| 2011/0294141 A1 | 12/2011 | Yamashita et al. |
| 2012/0065089 A1 | 3/2012 | Kuno et al. |
| 2012/0282612 A1 | 11/2012 | Yamashita et al. |
| 2014/0087395 A1 | 3/2014 | Takeuchi et al. |

FOREIGN PATENT DOCUMENTS

| WO | 2010/090264 A1 | 8/2010 |
| WO | 2010/100862 A1 | 9/2010 |
| WO | 2011/052244 A1 | 5/2011 |
| WO | 2012/133127 A1 | 10/2012 |

OTHER PUBLICATIONS

Hartig et al., "Wisteria floribunda agglutinin-labelled nets surround parvalbumin-containing neurons", Molecular Neuroscience, Oct. 1992, pp. 869-872, vol. 3, No. 10 (4 pages).
Ikehara et al., "Apical Golgi localization of N,N'-diacetyl-lactosediamine synthase, β4GalNAc-T3, is responsible for LacdiNAc expression on gastric mucosa", Glycobiology, 2006, pp. 777-785, vol. 16, No. 9 (9 pages).
Matsuda et al., "Wisteria floribunda Agglutinin-Positive Mucin 1 is a Sensitive Biliary Marker for Human Cholangiocarcinoma", Hepatology, 2010, pp. 174-182, vol. 52, No. 1 (9 pages).
Toyoshima et al., "A Phytomitogen from Wistaria floribunda Seeds and Its Interaction with Human Peripheral Lymphocytes", Biochemistry, 1971, pp. 4457-4463, vol. 10, No. 24 (7 pages).
Toyoshima et al., "Lectins from Wistaria floribunda Seeds and Their Effect on Membrane Fluidity of Human Peripheral Lymphocytes", The Journal of Biological Chemistry, 1975, pp. 1655-1660, vol. 250, No. 5 (6 pages).
Kurokawa et al., "Purification and Characterization of a Lectin from Wistaria floribunda Seeds", The Journal of Biological Chemistry, 1976, pp. 5686-5693, vol. 251, No. 18 (8 pages).
Cheung et al., "Purification and Properties of the Hemagglutinin from Wistaria floribunda Seeds", Biochemistry, 1979, pp. 1646-1650, vol. 18, No. 9 (5 pages).
Kaladas et al., "Purification and Properties of a Mitogenic Lectin from Wistaria floribunda Seeds", Biochemistry, 1979, pp. 4806-4812, vol. 18, No. 22 (7 pages).
Naito et al., "Expression of a Soybean (*Glycine max* [L.] Merr.) Seed Storage Protein Gene in Transgenic Arabidopsis thaliana and Its Response to Nutritional Stress and to Abscisic Acid Mutations", Plant Physiol., 1994, pp. 497-503, vol. 104, No. 2 (7 pages).
Tateno et al., "Glycoconjugate microarray based on an evanescent-field fluorescence-assisted detection principle for investigation of glycan-binding proteins", Glycobiology, 2008, pp. 789-798, vol. 18, No. 10 (10 pages).
Emanuelsson et al., "Locating proteins in the cell using TargetP, SignalP and related tools", Nature Protocols, 2007, pp. 953-971, vol. 2, No. 4 (19 pages).
Young et al., "The amino acid sequence of peanut agglutinin", Eur J Biochem, 1991, pp. 631-637, vol. 196, No. 3 (7 pages).
Adar et al., "Synthesis of soybean agglutinin in bacterial and mammalian cells", Eur J Biochem, 1997, pp. 684-689, vol. 249, No. 3 (6 pages).
Silva et al., "Purification and primary structure determination of a glactose-specific lectin from Vatairea guianensis Aublet seeds that exhibits vasorelaxant effect", Process Biochemistry, 2012, pp. 2347-2355, vol. 47 (9 pages).
International Search Report dated Mar. 4, 2014, issued in counterpart International Application No. PCT/JP2013/083854 (2 pages).

*Primary Examiner* — Karen Cochrane Carlson
(74) *Attorney, Agent, or Firm* — Westerman, Hattori, Daniels & Adrian, LLP

(57) ABSTRACT

[Problem] The purpose of the present invention is to stably supply high-quality and highly uniform *Wisteria floribunda* agglutinin (WFA) that recognizes biologically important sugar-chain markers, to elucidate the sugar-chain recognition activity in detail, and to furthermore increase the specificity of the sugar-chain recognition activity.
[Solution] The present invention involves the development of a technique for cloning genes for coding *Wisteria floribunda* agglutinin (WFA) and producing recombinant WFA having the same sugar-chain recognition activity as natural WFA from transformed bacteria. Natural WFA is reduced to thereby manufacture a reduced WFA monomer for specifically recognizing terminal GalNAc residue. A recombinant monomer WFA for recognizing LDN (GalNAcβ1, 4GlcNAc) sugar chain, which is important as a diagnostic marker among sugar chains having a terminal GalNAc residue, is manufactured by introducing cysteine mutation to recombinant WFA or by C-terminal-side amino acid deletion.

8 Claims, 13 Drawing Sheets

FIG. 1

```
ATGGCTAGCTCCCAAACTCAAAATTCATTCTCCGTTCTTCTATCCATTTCCTTAACTTTG    60
 M  A  S  S  Q  T  Q  N  S  F  S  V  L  L  S  I  S  L  T  L     20

TTCCTCTTGCTACTCAACAAGGTGAACTCAAAAGAAACAACTTCCTTTGTCTTCACCAGG   120
 F  L  L  L  N  K  V  N  S  K  E  T  T  S  F  V  F  T  R        40

TTTTCCCCAGACCCACAGAACTTGCTCCTCCAAGGTGACACCGTTGTTACCTCATCAGGG   180
 F  S  P  D  P  Q  N  L  L  Q  G  D  T  V  V  T  S  S  G        60

CATTTACAACTCACCCAGGTAAAGGACGGCGAACCAGTCTATAGTTCTCTTGGGCGAGCC   240
 H  L  Q  L  T  Q  V  K  D  G  E  P  V  Y  S  S  L  G  R  A     80

CTATATTATGCCCCTATCCACATTTGGGACAGCAACACCGACACCGTGGCTAACTTTGTC   300
 L  Y  Y  A  P  I  H  I  W  D  S  N  T  D  T  V  A  N  F  V    100

ACCAGCTTCTCCTTTGTCATCGATGCACCTAACAAAGCCAAAGCTGCAGATGGCCTTGCC   360
 T  S  F  S  F  V  I  D  A  P  N  K  A  K  A  A  D  G  L  A    120

TTCTTCCTTGCACCTGTGGATACTGAGCCCCAAAAACCTGGAGGACTGCTCGGGCTTTTC   420
 F  F  L  A  P  V  D  T  E  P  Q  K  P  G  G  L  L  G  L  F    140

CATGACGACCGTCACAATAAATCCAACCATATTGTTGCGGTTGAATTTGACACCTTCAAG   480
 H  D  D  R  H  N  K  S  N  H  I  V  A  V  E  F  D  T  F  K    160

AACAGCTGGGATCCAGAAGGTACACATATTGGAATCAATGTCAACTCTATCGTATCGAGA   540
 N  S  W  D  P  E  G  T  H  I  G  I  N  V  N  S  I  V  S  R    180

AAAACCACATCATGGGATTTGGAGAATGGCGAAGTAGCCAATGTTGTCATAAGCTACCAA   600
 K  T  T  S  W  D  L  E  N  G  E  V  A  N  V  V  I  S  Y  Q    200

GCTTCTACCAAAACCTTGACTGCCTCTTTGGTTTATCCTTCAAGTTCAACTAGTTATATC   660
 A  S  T  K  T  L  T  A  S  L  V  Y  P  S  S  T  S  Y  I       220

CTAAATGATGTTGTGGATTTGAAGCAAATTCTTCCCGAGTATGTAAGAGTTGGTTTCACC   720
 L  N  D  V  V  D  L  K  Q  I  L  P  E  Y  V  R  V  G  F  T    240

GCTGCAAGTGGACTATCTAAAGACCACGTTGAAACACACGATGTTCTTGCGTGGACTTTC   780
 A  A  S  G  L  S  K  D  H  V  E  T  H  D  V  L  A  W  T  F    260

GACTCAGATTTGCCAGATCCTAGCAGTGATGATTGCAACAACTTGCATCTTTCAAGCAAT   840
 D  S  D  L  P  D  P  S  S  D  D  C  N  N  L  H  L  S  S  N    280

GTTCTGCGCGGTTCCATCTAATTTCGAATGTGTTAGTTATGTGTGAGTGTGACCGAAGAA   900
 V  L  R  G  S  I  *                                            286

AACTATATATAATAAGACTTGCAACAACGATCGCTATCGTTTTGTGTAGAAACCGGTCAC   960

ACTATATGTGCCACTATAAAAAAAAAAAAAAAAAAAA                           996
```

FIG. 2

```
W. floribunda      -------MASSQTQNSFSVLLSISLTLFLLLLNKVNSKETTSFVPTRFSPDPQNLLLQGD
R. pseudoacacia    ------MASYNFKTQNSFPLLLSISF-PFLLLLNKVNSTGSLSFSFPKFAPNQPYLILQGD
C. kentukea        -ANSNSRPHLLQTQKPFSVVLAISITFYLLLLNKVNSEEALSFTFTKFVSNQDELLLQGD
S. Japonica        MATSNSRPHLLQTHKPFSVVLAISITFFLLLLNKVNSAEILSFSFPKFASNQEDLLLQGD
G. max             -----MATSKLKTQNVVVSLSLTLTLVLVLLTSKANSAETVSFSWNKPVPKQPNMILQGD
A. hypogaea        ------------MKPPCVFLTFPL-LLAASSKKVDSAETVSFNFNSFSEGNPAINPQGD
                               *  *      **  *      .   ***

W. floribunda      TVVTSSGHLQLTQVK-DGEPVYSSLGRALYYAPIHIWDSNTDTVANPVTSFSFVIDAPNK
R. pseudoacacia    ALVTSTGVLQLTNVV-NGVPSRKSLGRALYAAPPQIWDSTTGNVASFVTSFSFIIQAPNP
C. kentukea        ALVSSKGELQLTRVE-NGQPIPHSVGRALYSDPVHIWDSSTGSVASFVTSFTFVVEAPNE
S. japonica        ALVSSKGELQLTTVE-NGVPIWNSTGRALYYAPVHIWDKSTGRVASFATSFSFVVKAPVA
G. max             AIVTSSGKLQLNKVDENGTPKPSSLGRALYSTPIHIWDKETGSVASFAASFNFTFYAPDT
A. hypogaea        VTVLSNGNIQLTNLN-----KVNSVGRVLYAMPVRIWSSATGNVASFLTSFSFEMKDIKE
                    * *   **. .          * ** **  *  .**   *  ** * .** *

W. floribunda      AKAADXGLAFFPLAPVDTEP---QKPGG-LLGLFHDDRHNKSNHIVAVEFDTFKN--SWDPEG
R. pseudoacacia    ATTADGLAFFLAPVDTQP--LDLGG-MLGIFKNGYPNKSNQIVAVEFDTFSNR-HWDPTG
C. kentukea        NKTADGIAFFLAPPDTQV--QSLGG-PLGLFNSSVYNSSNQILAVEFDTFSN--SWDPTA
S. japonica        SKSADGIAFFLAPPNNQI--QGPGGGHLGLFHSSGYNSSYQIIAVDFDTHIN--AWDPNT
G. max             KPLADGLAFFLAPIDTKP--QTHAG-YLGLFNENESG--DQVVAVEFDTFRN--SWDPPN
A. hypogaea        YDPADGIIPFIAPEDTQIPAGSIGGGTLGVSDTKGAG---HFVGVEFDTYSNSEYNDPPT
                       ***. **.**  .          *  **.         .  . *.***   *   **

W. floribunda      THIGINVNSIVSRKTTSWDLENGEVANVVISYQASTKTLTASLVYPSSSTSYILNDVVDL
R. pseudoacacia    RHLGINVNSIKSVRTVPWNWTNGEVANVFISYEASTKSLTASLVYPSLETSFIVHAIVDV
C. Kentukea        RHIGIDVNSIESTRTATWGWRNGEVAIVLITYVAPAETLIASLTYPSSQTSYILSAAVDL
S. Japonica        RHIGIDVNSINSTKTVTWGWQNGEVANVLISYQAATETLTVSLTYPSSQTSYILSAAVDL
G. max             PHIGINVNSIRSIKTTSWDLAMNKVAKVLITYDASTSLLVASLVYPSQRTSNILSDVVDL
A. hypogaea        DHVGIDVNSVDSVKTVPWNSVSGAVVKVTVIYDSSTKTLSVAVTNDNG-DITTIAQVVDL
                    *.** ***.*  .*  *       .  *  .*  .*  .   **.

W. floribunda      KQILPEYVRVGFTAASGLSKDHVETHDVLAWTFDSDLPDPSS--DDCMNLHLSSNVLRGSI
R. Pseudoacacia    KDVLPEWVRFGPSATTGIDKGYVQTNDVLSWSFESNLPGGNSVASVKNAGLSTYAA----
C. kentukea        KSILPEWVRVGPSAATGRSAGYVETHDVLSWSFTSTLETGNSGAKQMNAHLASYALI---
S. japonica        KSILPEWVRVGPTAATGLTTQYVETHDVLSWSFTSTLETGDCGAKDDNVHLVSYAFI---
G. max             KTSLPEWVRIGPSAATGLDIP-GESHDVLSWSFASNLPHASS--NIDPLDLTSFVLHEAI
A. hypogaea        KAKLPERVKPGPSASGSLGGR--QIHLIRSWSFTSTLITTTRRSIDNNEKKIMNMASA--
                   *  *** *. **.*.           .  .*.* *
```

FIG. 3

FIG. 5
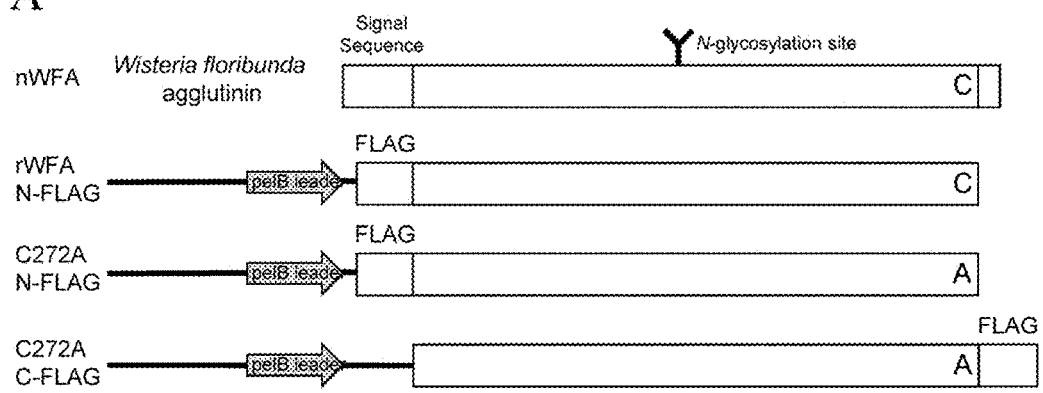
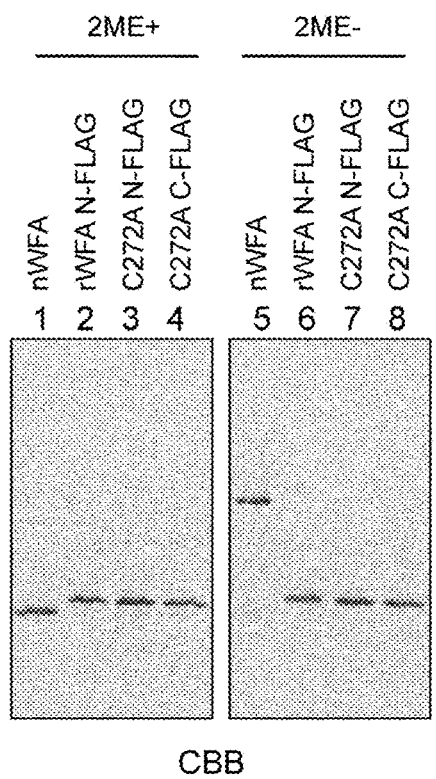
CBB

FIG. 7
A
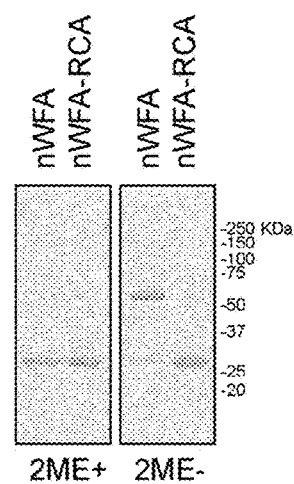
B
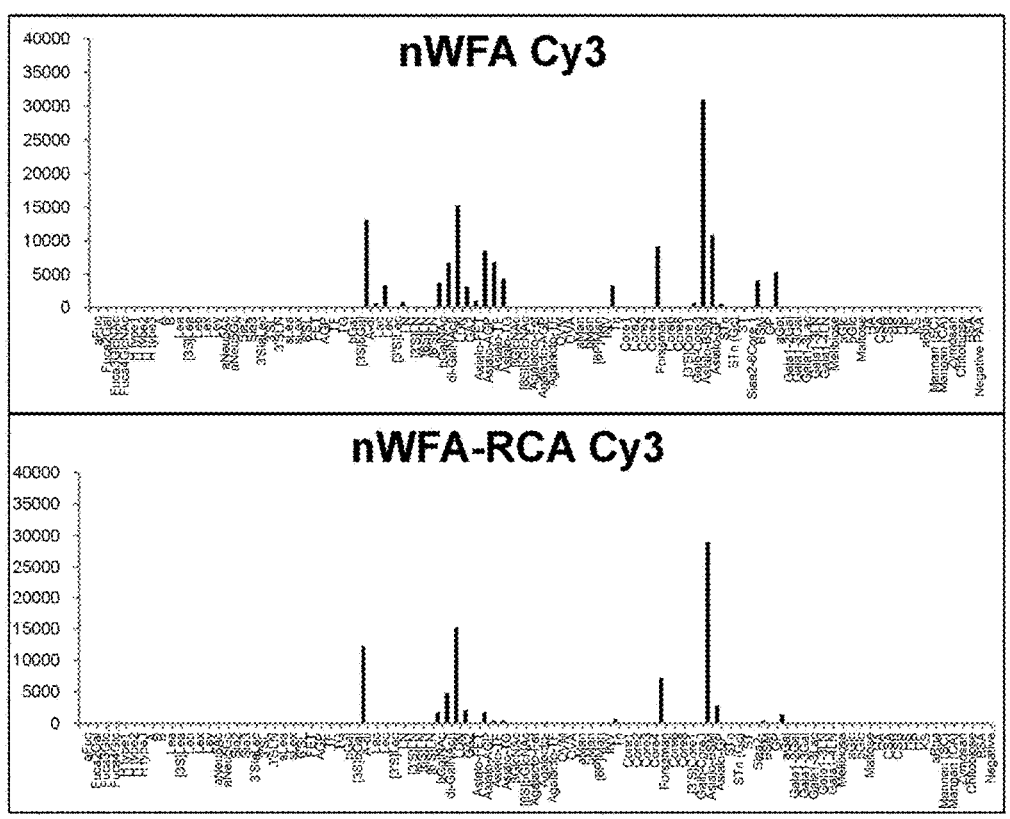

FIG. 8

| | | | | | |
|---|---|---|---|---|---|
| KETTSFVFTR | FSPDPQNLLL | QGDTVVTSSG | HLQLTQVKDG | EPVYSSLGRA | LYYAPIHIWD | 60
| SNTDTVANFV | TSFSFVIDAP | NKAKAADGLA | FFLAPVDTEP | QKPGGLLGLF | HDDRHNKSNH | 120
| IVAVEFDTFK | NSWDPEGTHI | GINVNSIVSR | KTTSWDLENG | EVANVVISYQ | ASTKTLTASL | 180
| VYPSSSTSYI | LNDVVDLKQI | LPEYVRVGFT | AASGLSKDHV | ETHDVLAWTF | DSDLPDPSSD | 240
| DCNNLHLSSN | VLRGSI | | | | | 256

| | |
|---|---|
| 2 – 10 | ETTSFVFTR |
| 11 – 38 | FSPDPQNLLLQGDTVVTSSGHLQLTQVK |
| 39 – 49 | DGEPVYSSLGR |
| 50 – 82 | ALYYAPIHIWDSNTDTVANFVTSFSFVIDAPNK |
| 85 – 102 | AADGLAFFLAPVDTEPQK |
| 85 – 114 | AADGLAFFLAPVDTEPQKPGGLLGLFHDDR |
| 103 – 114 | PGGLLGLFHDDR |
| 118 – 130 | SNHIVAVEFDTFK |
| 131 – 150 | NSWDPEGTHIGINVNSIVSR |
| 131 – 151 | NSWDPEGTHIGINVNSIVSRK |
| 152 – 174 | TTSWDLENGEVANVVISYQASTK |
| 175 – 198 | TLTASLVYPSSSTSYILNDVVDLK |
| 199 – 206 | QILPEYVR |
| 207 – 217 | VGFTAASGLSK |
| 218 – 243 | DHVETHDVLAWTFDSDLPDPSSDDCN |

FIG. 11

Supplementary Table 1. Glycans used for glycoconjugate microarray.

FIG. 12
A 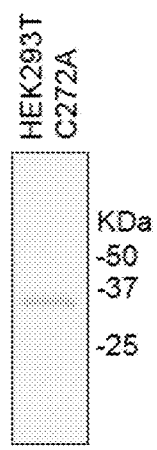
B 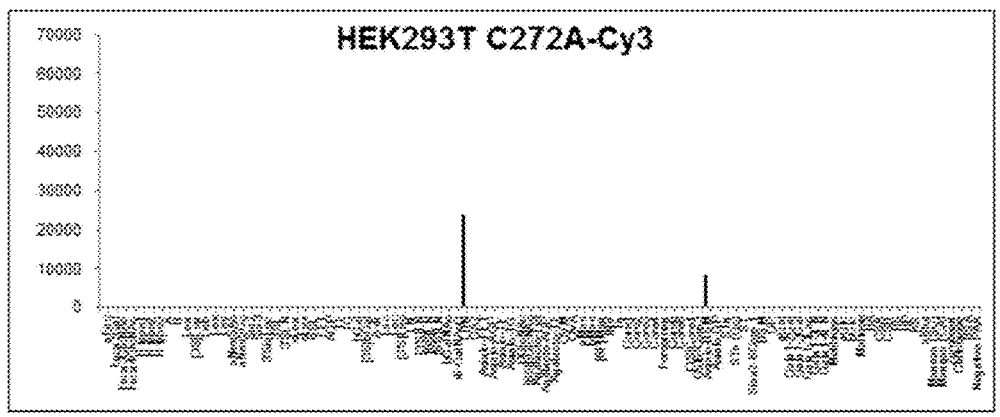

SEQUENCE LISTING

<160> NUMBER OF SEQ ID NOS: 16

<210> SEQ ID NO 1
<211> LENGTH: 861
<212> TYPE: DNA
<213> ORGANISM: wisteria floribunda
<220> FEATURE:
<223> OTHER INFORMATION: wisteria floribunda lectin

<400> SEQUENCE: 1
atggctagct cccaaactca aaattcattc tccgttcttc tatccatttc cttaactttg 60
ttcctcttgc tactcaacaa ggtgaactca aaagaaacaa cttcctttgt cttcaccagg 120
ttttccccag acccacagaa cttgctcctc caaggtgaca ccgttgttac ctcatcaggg 180
catttacaac tcacccaggt aaaggacggc gaaccagtct atagttctct tgggcgagcc 240
ctatattatg cccctatcca catttgggac agcaacaccg acaccgtggc taactttgtc 300
accagcttct cctttgtcat cgatgcacct aacaaagcca aagctgcaga tggccttgcc 360
ttcttccttg cacctgtgga tactgagccc caaaaacctg gaggactgct cgggcttttc 420
catgacgacc gtcacaataa atccaaccat attgttgcgg ttgaatttga caccttcaag 480
aacagctggg atccagaagg tacacatatt ggaatcaatg tcaactctat cgtatcgaga 540
aaaaccacat catgggattt ggagaatggc gaagtagcca atgttgtcat aagctaccaa 600
gcttctacca aaaccttgac tgcctctttg gtttatcctt caagttcaac tagttatatc 660
ctaaatgatg ttgtggattt gaagcaaatt cttcccgagt atgtaagagt tggtttcacc 720
gctgcaagtg gactatctaa agaccacgtt gaaacacacg atgttcttgc gtggactttc 780
gactcagatt tgccagatcc tagcagtgat gattgcaaca acttgcatct ttcaagcaat 840
gttctgcgcg gttccatcta a 861

<210> SEQ ID NO 2
<211> LENGTH: 286
<212> TYPE: PRT
<213> ORGANISM: wisteria floribunda

```
<220> FEATURE:
<223> OTHER INFORMATION: wisteria floribunda lectin

<400> SEQUENCE: 2

Met Ala Ser Ser Gln Thr Gln Asn Ser Phe Ser Val Leu Leu Ser Ile
1               5                   10                  15

Ser Leu Thr Leu Phe Leu Leu Leu Asn Lys Val Asn Ser Lys Glu
            20                  25                  30

Thr Thr Ser Phe Val Phe Thr Arg Phe Ser Pro Asp Pro Gln Asn Leu
            35                  40                  45

Leu Leu Gln Gly Asp Thr Val Val Thr Ser Ser Gly His Leu Gln Leu
        50                  55                  60

Thr Gln Val Lys Asp Gly Glu Pro Val Tyr Ser Ser Leu Gly Arg Ala
65                  70                  75                  80

Leu Tyr Tyr Ala Pro Ile His Ile Trp Asp Ser Asn Thr Asp Thr Val
                85                  90                  95

Ala Asn Phe Val Thr Ser Phe Ser Phe Val Ile Asp Ala Pro Asn Lys
            100                 105                 110

Ala Lys Ala Ala Asp Gly Leu Ala Phe Phe Leu Ala Pro Val Asp Thr
        115                 120                 125

Glu Pro Gln Lys Pro Gly Gly Leu Leu Gly Leu Phe His Asp Asp Arg
130                 135                 140

His Asn Lys Ser Asn His Ile Val Ala Val Glu Phe Asp Thr Phe Lys
145                 150                 155                 160

Asn Ser Trp Asp Pro Glu Gly Thr His Ile Gly Ile Asn Val Asn Ser
                165                 170                 175

Ile Val Ser Arg Lys Thr Thr Ser Trp Asp Leu Glu Asn Gly Glu Val
            180                 185                 190

Ala Asn Val Val Ile Ser Tyr Gln Ala Ser Thr Lys Thr Leu Thr Ala
        195                 200                 205

Ser Leu Val Tyr Pro Ser Ser Ser Thr Ser Tyr Ile Leu Asn Asp Val
210                 215                 220

Val Asp Leu Lys Gln Ile Leu Pro Glu Tyr Val Arg Val Gly Phe Thr
225                 230                 235                 240

Ala Ala Ser Gly Leu Ser Lys Asp His Val Glu Thr His Asp Val Leu
                245                 250                 255

Ala Trp Thr Phe Asp Ser Asp Leu Pro Asp Pro Ser Asp Asp Cys
            260                 265                 270

Asn Asn Leu His Leu Ser Ser Asn Val Leu Arg Gly Ser Ile
            275                 280                 285

<210> SEQ ID NO 3
<211> LENGTH: 23
<212> TYPE: DNA
<213> ORGANISM: Artificial
<220> FEATURE:
<223> OTHER INFORMATION: Fwd-1 primer

<400> SEQUENCE: 3
ctcttgctac tcaacaaggt gaa                                         23

<210> SEQ ID NO 4
<211> LENGTH: 22
<212> TYPE: DNA
<213> ORGANISM: Artificial
<220> FEATURE:
<223> OTHER INFORMATION: Rev-1 primer
```

```
<400> SEQUENCE: 4
caactctaac ccactccgga ag                                               22

<210> SEQ ID NO 5
<211> LENGTH: 27
<212> TYPE: DNA
<213> ORGANISM: Artificial
<220> FEATURE:
<223> OTHER INFORMATION: Adapter Primer-1

<400> SEQUENCE: 5
ccatcctaat acgactcact atagggc                                          27

<210> SEQ ID NO 6
<211> LENGTH: 23
<212> TYPE: DNA
<213> ORGANISM: Artificial
<220> FEATURE:
<223> OTHER INFORMATION: Adapter Primer-2

<400> SEQUENCE: 6
actcactata gggctcgagc ggc                                              23

<210> SEQ ID NO 7
<211> LENGTH: 22
<212> TYPE: DNA
<213> ORGANISM: Artificial
<220> FEATURE:
<223> OTHER INFORMATION: Rev-2 primer

<400> SEQUENCE: 7
actatagact ggttcgccgt cc                                               22

<210> SEQ ID NO 8
<211> LENGTH: 22
<212> TYPE: DNA
<213> ORGANISM: Artificial
<220> FEATURE:
<223> OTHER INFORMATION: Rev-3 primer

<400> SEQUENCE: 8
gggtgagttg taaatgccct ga                                               22

<210> SEQ ID NO 9
<211> LENGTH: 98
<212> TYPE: DNA
<213> ORGANISM: Artificial
<220> FEATURE:
<223> OTHER INFORMATION: WFA-HisFL-Fwd primer

<400> SEQUENCE: 9
ccatgggaca tcatcatcat catcacctcg actacaagga cgacgatgac aagggcaagc      60
ttgcggccgc gaattcaaaa gaaacaactt cctttgtc                              98

<210> SEQ ID NO 10
<211> LENGTH: 26
<212> TYPE: DNA
<213> ORGANISM: Artificial
<220> FEATURE:
<223> OTHER INFORMATION: WFA-Rev-1 primer

<400> SEQUENCE: 10
ctcgagttag atggaaccgc gcagaa                                           26
```

```
<210> SEQ ID NO 11
<211> LENGTH: 27
<212> TYPE: DNA
<213> ORGANISM: Artificial
<220> FEATURE:
<223> OTHER INFORMATION: C272A-Fwd primer

<400> SEQUENCE: 11
agcagtgatg atgccaacaa cttgcat                                         27

<210> SEQ ID NO 12
<211> LENGTH: 27
<212> TYPE: DNA
<213> ORGANISM: Artificial
<220> FEATURE:
<223> OTHER INFORMATION: C272A-Rev primer

<400> SEQUENCE: 12
agcagtgatg atgccaacaa cttgcat                                         27

<210> SEQ ID NO 13
<211> LENGTH: 51
<212> TYPE: DNA
<213> ORGANISM: Artificial
<220> FEATURE:
<223> OTHER INFORMATION: WFA-FLAG-Fwd primer

<400> SEQUENCE: 13
gaattcagac tacaaggacg acgatgacaa gaaagaaaca acttcctttg t              51

<210> SEQ ID NO 14
<211> LENGTH: 37
<212> TYPE: DNA
<213> ORGANISM: Artificial
<220> FEATURE:
<223> OTHER INFORMATION: WFA-Rev-2 primer

<400> SEQUENCE: 14
ggcctcgagt tagttgcaat catcactgct aggatct                              37

<210> SEQ ID NO 15
<211> LENGTH: 28
<212> TYPE: DNA
<213> ORGANISM: Artificial
<220> FEATURE:
<223> OTHER INFORMATION: WFA-Fwd-1 primer

<400> SEQUENCE: 15
ggaattcaaa agaaacaact tcctttgt                                        28

<210> SEQ ID NO 16
<211> LENGTH: 58
<212> TYPE: DNA
<213> ORGANISM: Artificial
<220> FEATURE:
<223> OTHER INFORMATION: WFA-FLAG-Rev primer

<400> SEQUENCE: 16
ctcgagttac ttgtcatcgt cgtccttgta gtcgttggca tcatcactgc taggatct       58
```

MODIFIED LECTIN DERIVED FROM WISTERIA FLORIBUNDA

TECHNICAL FIELD

The present invention relates to a technique for genetically producing *Wisteria floribunda* lectin (*Wisteria floribunda* agglutinin, WFA). In addition, the present invention relates to a method for manufacturing other novel modified lectins having sugar-chain recognition activity, which modifies some amino acids.

BACKGROUND ART

It is known that in a development or differentiation process, a sugar-chain structure reflects a cell state, and thus, is changed. Therefore, a considerable number of differentiation markers or cancer markers, which are now widely used, recognize a sugar chain. For example, a stage specific embryonic antigen 1 (SSEA1) that is a differentiation marker for a developmental state is an antibody to a sugar-chain structure, which is called Lewis X: Galβ1, 4GlcNAc (Fucα1,3)-, and the epitope of CA19-9 that is used as a colon cancer marker for a medical clinical service is a sugar-chain antigen, which is called sialyl Lewis A: SAα2, 3Galβ1, 3GlcNAc (Fucα1,4)-. The sugar chain of the cell surface as described above sensitively reflects a type of cell and a differentiation stage, and thus, it is easy to be a very available candidate for a biomarker.

As a method for detecting a disease-specific sugar-chain change, lectins, which are a sugar-chain binding protein derived from a plant or fungus, have been used along with an anti-sugar-chain antibody for a long time. When a tissue slice is stained with lectins, it is possible to separately stain the cells having different properties or the cells having different differentiation states, but since the sugar-chain recognizing specificity of the lectin is not clear, it is difficult to specify what kind of the sugar-chain structure is being modified. It is known that *wisteria floribunda* lectin (*Wisteria floribunda* agglutinin, WFA) that is one of plant lectins belongs to Leguminosae lectins, and recognizes a sugar chain including N-acetylgalactosamine (GalNAc) residue. However, the detailed specificity thereof is not clear. Nevertheless, the unique sugar-chain recognition specificity of WFA is used as a marker in various biological fields. For example, in the field of neuroscience, it is known that WFA is a classical marker for staining perineuronal network (PNN) (Non Patent Literature 1), and WFA also stains a normal foveolar epithelial cells of normal gastric mucosa (Non Patent Literature 2). It is also used in the identification method for identifying a prostate cancer and prostatic hypertrophy (Patent Literature 1). In addition, recently, the effectiveness of WFA as a biomarker that is used for diagnosis is highlighted, and thus, it is reported that WFA-positive MUC1 is a bile marker for diagnosing intrahepatic cholangiocarcinoma (Patent Literature 2 and Non Patent Literature 3).

The isolations of the lectin from *wisteria floribunda* seeds are reported by a plurality of groups in the 1970s (Table 1).

TABLE 1

|  | 1 | 2 | 3 | 4 | 5 |
|---|---|---|---|---|---|
| auther | Toyoshima S. | Toyoshima S. | Kurosawa T. | Cheung G. | Kaladas P. M. |
| year | 1971 | 1975 | 1976 | 1979 | 1979 |
| name | mitogen | hemagglutinin | agglutinin | hemagglutinin | mitogenic lectin |
| m.w. KDa (mono) | 32 | 34 | 32 | 28 | 32 |
| m.w. KDa (oligo) | 67 | 136 | 68 | 57 116 235 | 66 |
| oligomer | dimer | tetramer | dimer | dimer tetramer octamer | dimer |
| Ref. | (4) | (5) | (6) | (7) | (8) |

Toyoshima, and others report the isolations and biochemical analysis of two kinds of glycoprotein lectins having different molecular weights (WFM and WFH). *Wisteria floribunda* Mitogen (WFM) that forms the dimer of 67 KDa, in which the molecular weight of monomer is about 32 KDa, has hemagglutinating activity and phytogen activity (Non Patent Literature 4), but *Wisteria floribunda* hemagglutinin (WFH) of 136 KDa that is the tetramer of 35 KDa monomers does not have mitogen activity, but has strong hemagglutination activity and leukoagglutination activity as compared with WFM (Non Patent Literature 5). Meanwhile, the lectin purified by Kurokawa is a 68 KDa glycoprotein formed by the S—S bond of two 32 KDa subunits, and has hemagglutination activity inhibited by GalNAc (Non Patent Literature 6). For these two groups, each of the lectins is purified by a conventional biochemical isolation method of a protein, but for the group of Poretz and others, the homodimer lectin (Non Patent Literature 7) formed by the S—S bond between 28 KDa monomers having hemagglutination activity and the lectin having mitogen activity (66 KDa dimer formed by 32 KDa monomers) are isolated by the affinity to polyleucyl hog gastric mucin (Non Patent Literature 8). These lectins derived from *wisteria floribunda* seeds that are reported until now have similar property, such as, GalNAc recognition, but have subtle distinctions for amino acid compositions, sugar compositions, molecular weights, and the like. Therefore, it is difficult to determine whether or not the molecules are the same.

The WFA has grown in biological importance, but the sugar-chain recognition of WFA is not yet clear, and also, it is unclear whether the sugar-chain structures recognized by the WFAs in the neuron and stomach are the same or not. In addition, for the production of WFA, the WFAs that are sold by Vector Laboratory Company or EY Laboratory Company as a reagent are purified from natural *wisteria floribunda* seeds. Therefore, in order for the stable supply or in order to manage the uniformity among purification lots, it is required to shift the production thereof to the recombinant lectin production by a genetic engineering technique.

CITATION LIST

Patent Literature

Patent Literature 1: WO 2010/090264 A1
Patent Literature 2: WO 2010/100862 A1

Non Patent Literature

Non Patent Literature 1: Hartig, W., Brauer, K., and Bruckner, G. (1992) Neuroreport 3(10), 869-872
Non Patent Literature 2: Ikehara, Y., Sato, T., Niwa, T., Nakamura, S., Gotoh, M., Ikehara, S. K., Kiyohara, K., Aoki, C., Iwai, T., Nakanishi, H., Hirabayashi, J., Tatematsu, M., and Narimatsu, H. (2006) Glycobiology 16(9), 777-785
Non Patent Literature 3: Matsuda, A., Kuno, A., Kawamoto, T., Matsuzaki, H., Irimura, T., Ikehara, Y., Zen, Y., Nakanuma, Y., Yamamoto, M., Ohkohchi, N., Shoda, J., Hirabayashi, J., and Narimatsu, H. (2010) Hepatology 52(1), 174-182
Non Patent Literature 4: Toyoshima, S., Akiyama, Y., Nakano, K., Tonomura, A., and Osawa, T. (1971) Biochemistry 10(24), 4457-4463
Non Patent Literature 5: Toyoshima, S., and Osawa, T. (1975) J Biol Chem 250(5), 1655-1660
Non Patent Literature 6: Kurokawa, T., Tsuda, M., and Sugino, Y. (1976) J Biol Chem 251(18), 5686-5693
Non Patent Literature 7: Cheung, G., Haratz, A., Katar, M., Skrokov, R., and Poretz, R. D. (1979) Biochemistry 18(9), 1646-1650
Non Patent Literature 8: Kaladas, P. M., and Poretz, R. D. (1979) Biochemistry 18(22), 4806-4812
Non Patent Literature 9: Naito, S., Hirai, M. Y., Chino, M., and Komeda, Y. (1994) Plant Physiol 104(2), 497-503
Non Patent Literature 10: Tateno, H., Mori, A., Uchiyama, N., Yabe, R., Iwaki, J., Shikanai, T., Angata, T., Narimatsu, H., and Hirabayashi, J. (2008) Glycobiology 18(10), 789-798
Non Patent Literature 11: Emanuelsson, O., Brunak, S., von Heijne, G., and Nielsen, H. (2007) Nat Protoc 2(4), 953-971
Non Patent Literature 12: Young, N. M., Johnston, R. A., and Watson, D. C. (1991) Eur J Biochem 196(3), 631-637
Non Patent Literature 13: Adar, R., Streicher, H., Rozenblatt, S., and Sharon, N. (1997) Eur J Biochem 249(3), 684-689

SUMMARY OF INVENTION

Technical Problem

An object of the present invention is to achieve the stable supply and the uniformity among purification lots as well as the detailed elucidation of a sugar-chain recognition of a lectin WFA derived from *wisteria floribunda* seeds, which exhibits high biological importance. In this regard, another object is to provide recombinant lectin by a genetic engineering technique, and also, to provide WFA modifier having the modified sugar chain that is a recognized object by modifying the relevant recombinant lectin.

Solution to Problem

The present inventors succeeded in expressing a recombinant lectin in *E. coli* by cloning the gene encoding a *wisteria floribunda* lectin in cDNA derived from *wisteria floribunda* seeds. As a result of analyzing the sugar-chain binding activity of the recombinant WFA (rWFA), it could be confirmed that the recombinant WFA has the lectin activity that is the same as one available on the market. In addition, they found that when the natural WFA (nWFA) that is a dimer is made to be a monomer by treating the natural WFA with a reducing agent, the sugar-chain recognition specificity thereof is changed, thereby being lectin that recognizes GalNAc terminal sugar chain. In addition, they found that the rWFA prepared by introducing the mutation into the cysteine residue contributing to the formation of dimer specifically recognizes the LDN (GalNAcβ1, 4GlcNAc) sugar chain.

The present inventors completed the present invention by obtaining the above-described knowledge.

In other words, the present invention includes the following inventions.

[1] A polypeptide including any one of amino acid sequences represented by the following (1) or (2):

(1) an amino acid sequence represented by SEQ ID NO: 2, an amino acid sequence, in which one or several amino acids at the positions other than $272^{nd}$ position in the amino acid sequence is/are deleted, substituted, inserted, or added (except the case of deleting all of the amino acid sequences at the positions after $273^{rd}$ position or $274^{th}$ position); and (2) an amino acid sequence, in which any one of the amino acid sequences between N-terminal side and $30^{th}$ amino acid sequence of the amino acid sequences disclosed in (1) is deleted, the polypeptide having Gal/GalNAc terminal sugar-chain binding activity or GalNAc terminal sugar-chain binding activity.

[2] A nucleic acid encoding a polypeptide including the base sequence encoding any one of amino acid sequence represented by (1) or (2) disclosed in the above [1] and having Gal/GalNAc terminal sugar-chain binding activity.

[3] A nucleic acid encoding a polypeptide including any one of the base sequences represented by the following (1) or (2):

(1) a base sequence represented by SEQ ID NO: 1, or a base sequence that is hybridized with the complementary sequence thereof under a stringent condition, and a base sequence, in which $272^{nd}$ position on the amino acid sequence is the codon encoding Cys (except the case of deleting all the base sequences corresponding to the amino acid sequences at the positions after $273^{rd}$ position or $274^{th}$ position); and (2) a base sequence, in which the base sequence corresponding to any one of the amino acid sequences between N-terminal side and $30^{th}$ amino acid sequence of the base sequences disclosed in (1) is deleted, the polypeptide having Gal/GalNAc terminal sugar-chain binding activity.

[4] A polypeptide including any one of amino acid sequences represented by the following (1) to (6):

(1) an amino acid sequence, in which $272^{nd}$ amino acid in the amino acid sequence represented by SEQ ID NO: 2 is an amino acid other than Cys;

(2) an amino acid sequence, in which one or several amino acids at the positions other than $272^{nd}$ position in the amino acid sequence disclosed in (1) is/are deleted, substituted, inserted, and added;

(3) an amino acid sequence, in which the amino acids between C-terminal side and any one of 13 to $15^{th}$ amino acids in the amino acid sequence represented by SEQ ID NO: 2 are deleted;

(4) an amino acid sequence, in which one or several amino acids in the amino acid sequence disclosed in (3) is/are deleted, substituted, inserted, or added;

(5) an amino acid sequence, in which $272^{nd}$ position in the amino acid sequence represented by SEQ ID NO: 2 is alkylated Cys, or an amino acid sequence, in which one or several amino acids at the positions other than $272^{nd}$ position in the amino acid sequence is/are deleted, substituted, inserted, or added; and (6) an amino acid sequence, in which any one of amino acid sequences between N-terminal side and $30^{th}$ amino acid sequence in any one of the amino acid sequences disclosed in (1) to (5) is deleted, the polypeptide specifically recognizing a GalNAc terminal sugar chain.

[5] A polypeptide including any one of amino acid sequences represented by the following (1) to (5):

(1) an amino acid sequence, in which an amino acid at $272^{nd}$ position in the amino acid sequence represented by SEQ ID NO: 2 is an amino acid other than Cys;

(2) an amino acid sequence, in which one or several amino acids at the positions other than $272^{nd}$ position in the amino acid sequence disclosed in (1) is/are deleted, substituted, inserted, or added;

(3) an amino acid sequence, in which the amino acids between C-terminal side and any one of 13 to $15^{th}$ amino acids in the amino acid sequence represented by SEQ ID NO: 2 are deleted;

(4) an amino acid sequence, in which one or several amino acids in the amino acid sequence disclosed in (3) is/are deleted, substituted, inserted, or added; and (5) an amino acid sequence, in which any one of amino acid sequences between N-terminal side and $30^{th}$ amino acid sequence in any one of the amino acid sequences disclosed in (1) to (4) is deleted, the polypeptide having LDN-specific sugar-chain recognition ability among GalNAc terminal sugar chains.

[6] A nucleic acid encoding a polypeptide including the base sequence encoding any one of the amino acid sequences of (1) to (5) disclosed in the above [5], which specifically recognizes a LDN sugar chain.

[7] A nucleic acid encoding a polypeptide including any one of the base sequences represented by the following (1) to (4):

(1) a base sequence, in which the codon corresponding to $272^{nd}$ amino acid in the base sequence represented by SEQ ID NO: 1 is an amino acid other than Cys;

(2) a base sequence that is hybridized with the complementary sequence of the base sequence disclosed in (1) under a stringent condition, and a base sequence, in which the codon corresponding to $272^{nd}$ amino acid is an amino acid other than Cys;

(3) a base sequence, in which the base sequence corresponding to any one of amino acids between 3'-terminal side and C-terminal 13 to $15^{th}$ amino acids in the base sequence represented by SEQ ID NO: 1 is deleted; and (4) a base sequence, in which the base sequence corresponding to any one of amino acid sequences between 5' side and N-terminal amino acid to $30^{th}$ amino acid in any one of the base sequences disclosed in (1) to (3) is deleted, the nucleic acid specifically recognizing a LDN sugar chain.

[8] An expression vector including the nucleic acid disclosed in the above [2], [3], [6], or [7].

[9] A transformed cell being transformed by using the nucleic acid disclosed in the above [2], [3], [6], or [7].

[10] A method for preparing a polypeptide having Gal/GalNAc terminal sugar-chain binding activity, GalNAc terminal sugar-chain binding activity or LDN sugar-chain-specific binding activity, the method including performing collection from the culture product obtained by culturing the transformed cells disclosed in the above [9].

[11] A reagent for specifically detecting a Gal/GalNAc terminal sugar chain or GalNAc terminal sugar chain, the reagent including the polypeptide disclosed in the above [1] or [4].

[12] A reagent for specifically detecting a LDN sugar chain, the reagent including the polypeptide disclosed in the above [5].

[13] A method for changing sugar-chain binding activity into GalNAc terminal sugar-chain-specific binding activity, the method including:

reducing the polypeptide that forms a dimer and includes the amino acid sequence represented by the following (1) or (2) having Gal/GalNAc terminal sugar-chain binding activity:

(1) an amino acid sequence represented by SEQ ID NO: 2, or an amino acid sequence, in which one or several amino acids at the positions other than $272^{nd}$ position in the amino acid sequence is/are deleted, substituted, inserted, or added; and (2) an amino acid sequence, in which any one of the amino acid sequences between N-terminal side and $30^{th}$ amino acid sequence of the amino acid sequences disclosed in (1) is deleted; and alkylating Cys in the amino acid sequence.

[14] A method for changing sugar-chain binding activity into LDN sugar-chain-specific binding activity, the method including:

substituting Cys at $272^{nd}$ position in the polypeptide that forms a dimer and includes the amino acid sequence represented by the following (1) or (2) having Gal/GalNAc terminal sugar-chain binding activity by other amino acids:

(1) an amino acid sequence represented by SEQ ID NO: 2, or an amino acid sequence, in which one or several amino acids at the positions other than $272^{nd}$ position in the amino acid sequence is/are deleted, substituted, inserted, or added; and (2) an amino acid sequence, in which any one of the amino acid sequences between N-terminal side and $30^{th}$ amino acid sequence of the amino acid sequences disclosed in (1) is deleted; or deleting any one of amino acids between C-terminal side and 13 to $15^{th}$ amino acids of the amino acid sequence.

Advantageous Effects of Invention

Since a recombinant WFA (rWFA) can be provided according to the present invention, it is possible to mass-produce a stable-quality WFA lectin having sugar-chain binding activity to a terminal GalNAc residue and Gal residue, like a natural WFA by transformed cells.

In addition, the WFA monomer prepared by the reduction of the natural WFA, which is provided by the present invention, is a WFA lectin that does not recognize a Gal residue, but specifically recognizes only a GalNAc residue, and the WFA monomer prepared by the cysteine modification of the recombinant WFA (rWFA) is a WFA lectin that specifically recognizes only LDN (GalNAcβ1, 4GlcNAc) sugar chain among the sugar chains having the terminal GalNAc residue. As described above, according to the present invention, it is possible to provide a WFA lectin having modified sugar-chain recognizability that has extremely high usefulness.

BRIEF DESCRIPTION OF DRAWINGS

FIG. 1 illustrates a base sequence of *wisteria floribunda* lectin (WFA) gene, and it is expected that the estimated amino acid sequence N-terminal 30 amino acid is a signal sequence. It is expected that N-linked glycosylation is occurred at $146^{th}$ asparagine (N). It is considered that there is a possibility of processing C-terminal 13-amino acid.

FIG. 2 illustrates an amino acid sequence alignment of a leguminous plant lectin.

FIGS. 3A to 3C illustrate the expression of recombinant WFA (rWFA) in *E. coli*. FIG. 3A illustrates the construction of plasmid for expressing rWFA and C272A modifier in *E. coli*. The N-terminal signal sequence was substituted with Hisx6+FLAG sequence, and the gene was inserted into the downstream of pelB leader (secretion signal in periplasm). It was introduced into *E. coli* BL21-CodonPlus (DE3)-RIPL to obtain transformant. FIG. 3B illustrates the confirmation of recombinant protein expression by an anti-FLAG antibody. As a result, it could be confirmed that the recombinant protein is leaked out in a culture medium other than a periplasm fraction, and thus, exists. FIG. 3C illustrates the purification from the culture supernatant of the recombinant protein using an anti-FLAG antibody column. On the SDS-PAGE under the reducing condition, it was confirmed that the rWFA was observed as a single band at 31 KDa (lane 2) and the WFA available on the market (nWFA) was observed as a single band at 28 KDa (lane 1). Under the non-reducing condition, it was confirmed that the nWFA existed as a single band at about 60 KDa (lane 4) and for the rWFA, about half and half of the dimer and monomer existed (lane 5). Meanwhile, the mutant (C272A) was confirmed as a single band in the size of the monomer under both of the reducing and non-reducing conditions, and thus, it was confirmed that no dimers were formed. From this result, it was clear that Cys at $272^{nd}$ position is essential for forming a dimer.

FIGS. 5A and 5B illustrate the expression of the recombinant WFA without C-terminal 13-amino acid. FIG. 5A illustrates the construction of plasmid for expressing the recombinant WFA without C-terminal 13-amino acid. The plasmid for expressing the rWFA without C-terminal 13-amino acid and also with a FLAG tag at N terminus or C terminus was constructed. FIG. 5B illustrates the result of detecting proteins by a Coomassie Brilliant Blue (CBB) staining. When 13-amino acid was deleted, a dimer was hardly formed. The dimer was not detected with the CBB staining.

FIGS. 7A and 7B illustrate the analysis of the sugar-chain binding activity of a monomer nWFA. FIG. 7A illustrate the construction of nWFA monomer by the reduction. The monomer nWFA was manufactured by reducing the S—S bond contributing to the formation of dimer, and then, performing the alkylation thereof. It was confirmed from the SDS-PAGE under the non-reducing condition that it was a monomer. As illustrated in FIG. 7B, it was confirmed that the monomerized nWFA lost the sugar-chain binding activity to Gal, and thus, specifically recognized GalNAc terminal sugar chain.

FIG. 8 illustrates the analysis of amino acids of a natural WFA.

FIG. 11 illustrates the examples of sugar chain types on a glycan array.

FIGS. 12A and 12B illustrate the purified C272A modified rWFA (with N-glycan) produced by mammalian cells. FIG. 12A illustrates the confirmation of monomer expression by SDS-PAGE (the increase in molecular weight by the influence of sugar chain). FIG. 12B illustrates the analysis of sugar-chain binding specificity by a GP array.

FIG. 13A illustrates the confirmation of monomer expression by SDS-PAGE. FIG. 13B illustrates the analysis of sugar-chain binding specificity by a GP array.

DESCRIPTION OF EMBODIMENTS

Figure 4:
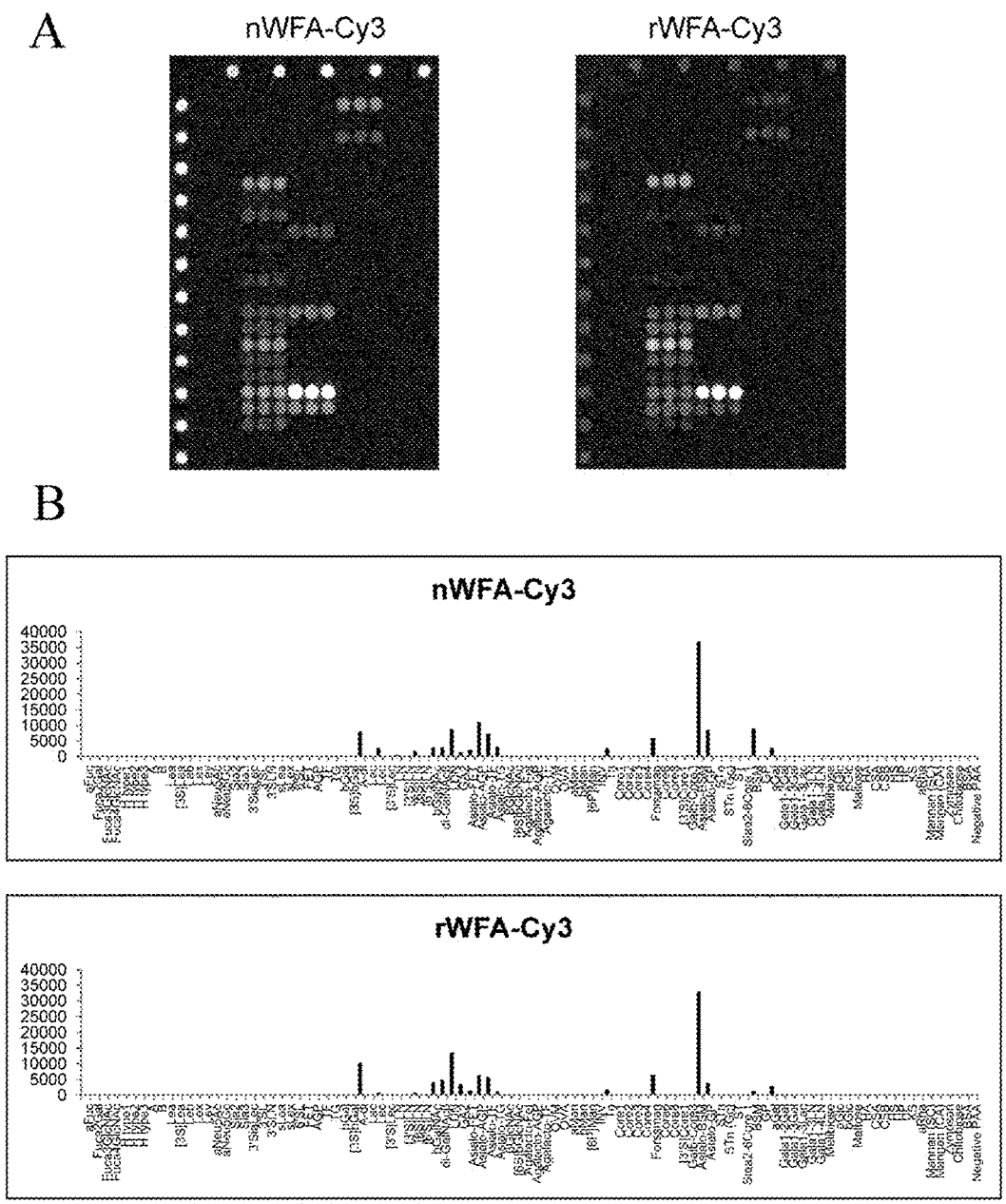
FIG. 4 illustrates the comparison between the sugar-chain binding activities of a natural WFA and a recombinant WFA using a glycoprotein array. (A) Cy3 label nWFA and rWFA on a glycoprotein array. (B) The verification of sugar-chain recognition specificities of nWFA and rWFA. As a result, the nWFA and rWFA exhibited very similar sugar-chain recognition specificity. Asialo-BSM (bovine submaxillary mucin) exhibited the strongest signal to both of them, and exhibited the binding ability to Gal terminus (asialo-AGP or asialo-TF) along with the sugar chain of GalNAc terminus (A-di, βGalNAc, di-GalNAcβ, LDN, GA2, Tn, Forssman).

1. *Wisteria floribunda* Lectin (WFA) and Recombinant Modifier Thereof 1-1. Lectin Derived from *Wisteria Floribunda* Seeds Cloned According to the Present Invention and Recombinant Lectin Thereof In the present invention, we succeeded in cloning the genes of lectin derived from *wisteria floribunda* seeds that were used as a tissue marker for a long time and in manufacturing recombinant lectin.

The cloned gene encodes new protein composed of 286 amino acids (FIG. 1, SEQ ID NOS: 1 and 2), and the expected molecular weight of a maturing lectin domain (aa31-273) without the domain having the processing possibility of C-terminus or signal sequence of N-terminus was 26.6 KDa. Since the possibility of adding one N-glycan in the seeds is considered, about 1.3 KDa is added to the expected molecular weight thereof, and thus, the expected molecular weight is to be 27.9 KDa. Therefore, the expected molecular weight is well matched with the molecular weight of the WFA lectin available on the market. In addition, from the result of analyzing the shotgun peptide sequence of the WFA available on the market by a LC/MS method, the lectin which is cloned this time is almost the same as the WFA available on the market, but when being compared with the WFA available on the market, which is purified from natural substances, it is the polypeptide having C-terminus added with 13-amino acid. For other leguminosae lectins, such as, peanut agglutinin (PNA), there is reported the example having C-terminus that is processed (Non Patent Literature 12). Therefore, it is considered that for the natural WFA, C-terminal 13-amino acid is subjected to a processing.

In other words, the present invention provides new recombinant WFA (rWFA) that is called a "precursor WFA" before being subjected to the processing of C-terminal amino acid in a natural WFA. In the present invention, "rWFA" is added with 13-amino acid at the C-terminal side as compared with a natural WFA, and also, indicates "recombinant WFA" with or without N-terminal 30-amino acid that is a signal sequence.

The molecular weight and amino acid composition of the lectin which is cloned this time are similar to those of the lectin reported by Kurokawa (Non Patent Literature 6) or Cheung (Non Patent Literature 7) until now, but are not completely matched with the molecular weight and amino acid composition of *wisteria floribunda* lectin WFH (Non Patent Literature 5), in which the purification thereof is reported by Toyoshima, and others. These differences may be generated by the analyzing method differences, and also, it can be considered that there is a possibility that more lectins or mitogens exist in the *wisteria floribunda* seeds.

1-2. Dimer Ability of Recombinant Lectin and Modifier Thereof

This time, the rWFA that is expressed in *E. coli* is, unlike a natural WFA (nWFA), a precursor without a sugar chain and with 13-amino acid at the C-terminal side, at least. However, it was confirmed that the rWFA has the same sugar-chain recognition activity as the natural WFA. It is expected that the natural WFA has one N-glycan, and as for the amino acid sequence thereof, the only N-glycan (N-linked sugar chain) binding position is asparagine (N) at $146^{th}$ position. However, since the rWFA without a sugar chain has the activity, it is considered that the sugar chain is unnecessary for the activity. It is reported that the addition of N-glycan in soybean agglutinin (SBA) that belongs to a leguminosae lectin family does not contribute to the activity or the formation of polymer (Non Patent Literature 13), and the same tendency even in WFA is confirmed. The nWFA forms a dimer by a disulfide bond, but it is strongly considered by determining the amino acid sequence that the only cysteine at $272^{nd}$ has the possibility of contributing to the formation of disulfide bond. When the WFA is expressed in the periplasm of *E. coli*, the about half of the rWFA purified from a nutrient medium may form a dimer, but C272A that is a modifier, in which the cycteine is substituted by alanine, does not form a dimer. Therefore, it is considered that the above-described possibility is the right one. When it is assumed that 13-amino acid at C-terminus is subjected to a processing during the maturing process of protein, the maturing nWFA proteins almost form a dimer at C-terminus. We attempted the expression of the recombinant lectin, in which 13-amino acid at C-terminus is excluded in advance, but the expression amount thereof is quite the same as the case of including 13-amino acid. Nevertheless, the dimer is almost not formed. For this reason, it is considered that after forming a dimer during the maturing process of WFA protein, the processing at C-terminus may occur.

In addition, even though the cysteine is not included in the lectin sequence belonging to Leguminosae, such as, SBA or PNA, when being expressed in *E. coli*, the polymer may be formed by a noncovalent bond, but in the case of WFA, the point capable of forming a disulfide bond because of including cysteine is different from the above-described lectin. There is cysteine at the position close to WFA in the sequence of *Sophora Japonica* agglutinin (SJA) (FIG. 2), and thus, it is also suggested that the cysteine has the possibility of contributing to the formation of dimer.

1-3. WFA Monomerization and Sugar-Chain Binding Specificity in Recombinant Lectin Modifier This time, the rWFA is expressed and purified in *E. coli*, and the sugar-chain binding specificity thereof is investigated using a glycan array. As a result, the rWFA exhibits the sugar-chain binding specificity to Gal/GalNAc, like the natural one. However, C272A that is a modifier of the cysteine residue at $272^{nd}$ contributing to the formation of dimer or nWFA-RCA that is a monomer prepared by performing the reduction and alkylation of nWFA that is a dimer has the changed sugar-chain binding specificity. Therefore, it is considered that the formation of dimer through the cysteine is important to recognize Gal/GalNAc by a nature-derived WFA. Meanwhile, the nWFA-RCA that is the monomer of nWFA specifically recognizes the sugar-chain of GalNAc terminus, but does not recognize the sugar chain of Gal terminus other than that. It is reported by Kurokawa and others that the binding activities of a monomer and a dimer to GalNAc are not changed (Non Patent Literature 6). However, it is clear from these results that the recognition activity is not changed to the overall sugar chain including GalNAc at terminus as well as GalNAc. The cysteine residue exists at almost C-terminus of the maturing WFA, and thus, it is expected that it is not involved in the formation of sugar-chain binding pocket of lectin. However, the dimer is formed, and thus, Gal terminal sugar-chain binding activity is generated. It is unclear that the nWFA recognize GalNAc and Gal as the same pocket, or new sugar-chain recognition site for recognizing Gal by forming a dimer is generated. However, when the structure thereof is confirmed by crystallizing it and analyzing the structure through an X-ray structure analysis, the molecule mechanism of sugar-chain binding may be confirmed.

Figure 3:
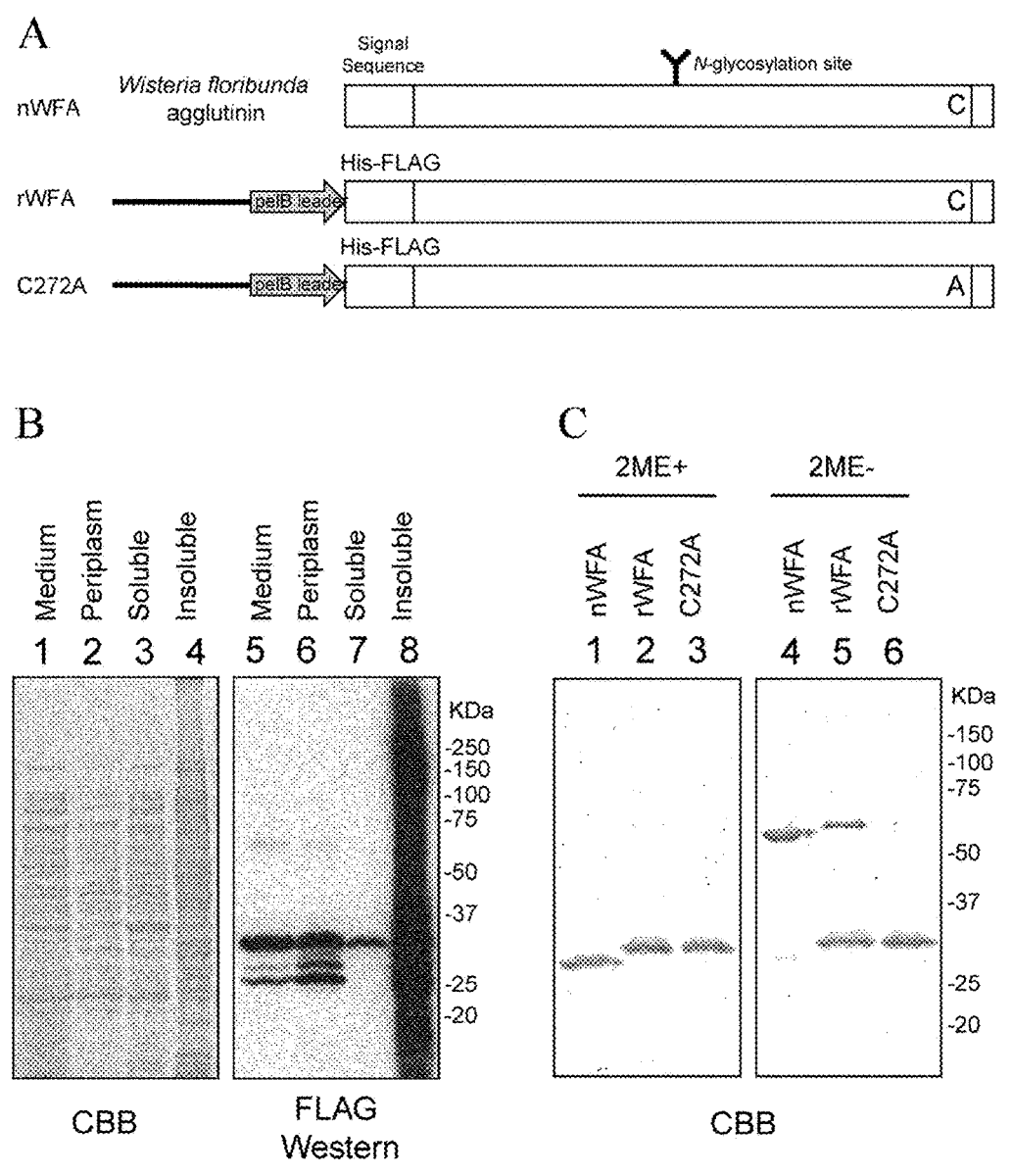

In addition, the rWFA C272A surprisingly has very limited sugar-chain binding activity, that is, LDN-specific recognition activity. As illustrated in FIG. 3C, when the rWFA is purified from a culture medium, about half thereof forms a dimer through a cysteine residue, and thus, like the nWFA, exhibits Gal/GalNAc binding activity. The modification of cysteine residue of rWFA C272A does not affect the sugar-chain binding pocket, but does not form a dimer during the synthesizing process of protein, and thereby, there may be the possibility of affecting the structure and stability other than the pocket.

This time, the gene encoding the WFA lectin is isolated, and then, the recombinant WFA having modified amino acid sequence is genetically manufactured. As a result, it is confirmed that a plurality of sugar-chain binding specificities of WFA converge in LDN. It is exhibited that there is the possibility of solving the extensive sugar-chain recognition specificity that is one of lectin defects by the gene modification. It is expected that since there is the possibility of changing the recognition specificity with an evolution engineering technique by using them for a mold in future, a useful modified lectin may be developed as a diagnosis biomarker or tissue and a cell marker for various diseases in future.

2. As for WFA Gene of the Present Invention and Expression Product Thereof

The new recombinant WFA (rWFA) provided in the present invention includes any one of the amino acid sequences represented by the following (1) or (2), and also, may be expressed as the polypeptide having a binding activity to GalNAc terminal sugar chain along with Gal terminal sugar chain (hereinafter, referred to as Gal/GalNAc terminal sugar-chain binding activity) or GalNAc terminal sugar-chain binding activity. Here, the rWFA forming a dimer has Gal/GalNAc terminal sugar-chain binding activity, and the rWFA of monomer has LDN-specific binding activity among the GalNAc terminal sugar chains.

(1) The amino acid sequence represented by SEQ ID NO: 2, or the amino acid sequence, in which one or several amino acids at the positions other than $272^{nd}$ position in the amino acid sequence is/are deleted, substituted, inserted, or added (except the case of deleting all of the amino acid sequences at the positions after $273^{rd}$ position or $274^{th}$ position), and (2) The amino acid sequence, in which one amino acid sequence among the amino acid sequences between N-terminal side and $30^{th}$ amino acid sequence of the amino acid sequences represented by the above (1) is deleted.

In addition, the several numbers of the amino acids means 1 to 20, preferably 1 to 10, and more preferably 1 to 5.

Therefore, the base sequence of rWFA gene may be a base sequence encoding the amino acid sequence disclosed in the above (1) or (2), but the base sequence may be also represented by the following (3) or (4).

(3) The base sequence represented by SEQ ID NO: 1 or the base sequence that is subjected to a hybridization with a complementary sequence thereof under a stringent condition, and also, the base sequence, in which the position at $272^{nd}$ on the amino acid sequence is a codon encoding Cys (except the case of deleting all of the base sequences corresponding to the amino acid sequences at the positions after $273^{rd}$ or $274^{th}$ position), and (4) The base sequence, in which the base sequence corresponding to any one of amino acid sequence among the amino acid sequences between N-terminal side and $30^{th}$ amino acid sequence in the base sequences represented by the above (3) is deleted.

In addition, the stringent condition means a shrinkage condition that can be subjected to the hybridization of the sequence having 85% or more, preferably 90% or more, and more preferably 95% or more of the identity for a general hybridization method.

When the expression vector for expressing the WFA gene of the present invention is constructed, a secretion signal is particularly unnecessary, but in order to purify an expressed product, it is easy and efficient that the secretion signal is allowed to be secreted in a nutrient medium, and then, the nutrient medium is purified, and thereby the secretion signal is preferably added.

The transformed host for preparing the recombinant WFA of the present invention may be eukaryotic cells, such as, mammal cells, insect cells, plant cells, or yeast. However, the fucose-containing sugar chain that is originally included in a natural substance is not involved in the sugar-chain recognition function of WFA lectin, and thus, it is preferable to use prokaryotic cell host, such as, *E. coli*.

For the obtained recombinant WFA, a general purifying method may be applied, and for example, the purification using a general tag or an affinity column to the sugar-chain ligand may be used for purifying the recombinant WFA.

The recombinant WFA (rWFA) obtained according to the present invention forms a monomer along with a dimer in the almost same amount as the natural WFA. The dimerized rWFA exhibits the extensive sugar-chain recognition ability that is almost the same as the natural WFA, but the rWFA in the state of monomer has LDN-specific sugar-chain recognition ability such as the recombinant WFA modifier to be described below. The relevant rWFA monomer may be isolated from a dimer by the technique, such as, a gel filtration.

3. Recombinant WFA Modifier Having LDN-Specific Sugar-Chain Recognition Ability in the Present Invention (3-1) Recombinant WFA Modifier by Introducing the Mutation into Cys at $272^{nd}$ Position of rWFA (c272rWFA)

In the present invention, "LDN-specific sugar-chain recognition ability" means a sugar-chain recognition ability that does not recognize Gal terminal sugar chain, but recognizes only the case of having GalNAcβ1, 4GlcNAc sugar chain among GalNAc terminal sugar chains. Specifically, it is possible to detect the LDN sugar-chain marker that is known to be expressed at a normal stomach epithelial cell, and the like.

Among the recombinant WFA modifiers having LDN specificity that is developed in the present invention, the recombinant WFA modifier by the mutation introduction into Cys at $272^{nd}$ position (C272 modified rWFA) has the amino acid sequence, in which Cys at $272^{nd}$ position is substituted by other amino acid, and does not form a dimer. As a result, it is a WFA lectin having LDN-specific sugar-chain recognition ability, and may be expressed as follows.

A polypeptide having any one of amino acid sequence represented by the following (1) to (3):

(1) an amino acid sequence, in which the amino acid at $272^{nd}$ position in the amino acid sequence represented by SEQ ID NO: 2 is an amino acid other than Cys;

(2) an amino acid sequence, in which one or several amino acids at the positions other than $272^{nd}$ position in the amino acid sequence represented by the above (1) is/are deleted, substituted, inserted, or added; and (3) an amino acid sequence, in which any one of the amino acid sequences between N-terminal side and $30^{th}$ amino acid in the amino acid sequence represented by the above (1) or (2) is deleted, and the polypeptide having LDN-specific sugar-chain recognition ability.

In addition, the several numbers means 1 to 20, preferably 1 to 10, and more preferably 1 to 5.

In addition, it may be any amino acids as long as the amino acid at $272^{nd}$ position in the amino acid sequence of (1) is the amino acids other than Cys, but the amino acids having a reacting group, such as Ala or Gly are preferable, and Ala is more preferable.

In addition, the relevant recombinant WFA modified gene (C272rWFA gene) may be the base sequence encoding the amino acid sequences represented by the above (1) to (3), but the base sequence may be represented by any one of the base sequences represented by the following (4) to (6).

(4) the base sequence, in which the codon corresponding to the amino acid at $272^{nd}$ position in the base sequence represented by SEQ ID NO: 1 is the amino acids other than Cys, (5) the base sequence that is subjected to the hybridization with the complementary sequence of the base sequence represented by the above (4) under a stringent condition, and the base sequence, in which the codon corresponding to the amino acid at $272^{nd}$ position is the amino acids other than Cys, (6) the base sequence, in which the base sequence corresponding to any one of amino acid among the amino acids between 5' side and N-terminal amino acid to $30^{th}$ amino acid in the base sequence represented by the above (4) or (5) is deleted.

In addition, the stringent condition means a shrinkage condition, in which the sequence having 85% or more, preferably 90% or more, and more preferably 95% or more of the identity in a general hybridization method can be hybridized.

In addition, according to the present invention, for the recombinant WFA modifier (C272 modified rWFA), further, the recombinant WFA modifier of C272, N146Q modified rWFA, in which asparagines at $146^{th}$ position that is a N-type sugar-chain binding position is modified with glutamine (N146Q), is manufactured. It is confirmed that the relevant modifier does not have a sugar chain and has the same "LDN-specific sugar-chain recognition ability" as the case of the recombinant WFA modifier (C272 modified rWFA) expressed in *E. coli*, even in the case of using yeast or mammal cells other than bacteria, such as, *E. coli* as a host.

(3-2) Recombinant WFA Modifier (rWFA Delta) by the Deletion of C-Terminal Side

The dimer at C272 position is not formed by deleting the partial amino acid sequence at C-terminal side of the dimer recombinant WFA, and thus, it is possible to perform the monomerization. The sugar-chain recognition ability of the monomer is the same as C272 rWFA, and the LDN sugar-chain specificity is exhibited. Even though the natural WFA does not have the amino acid sequence ($275^{th}$ to $293^{rd}$ positions) after $13^{th}$ position of C-terminal side of the recombinant WFA, the dimer by the S—S bond at $272^{nd}$ Cys position is formed. For this reason, it may be assumed that the proteins in the natural WFA are biosynthesized, and 13-amino acid part at $275^{th}$ position or less after forming the dimer is processed. Meanwhile, it is confirmed that in the case of the recombinant WFA, in which the amino acids from C-terminus to $13^{th}$ amino acid are deleted in advance, $272^{nd}$ Cys corresponding to $15^{th}$ position loses the ability of forming a dimer; thus, is subjected to the monomerization; and also, achieves LDN sugar-chain specificity that is the equivalent to C272rWFA (FIGS. 3A to 3C). It is considered that when $272^{nd}$ Cys and the neighboring amino acid sequence thereof are removed, the monomer having the same LDN sugar-chain specificity may be formed. In other words, when it is the recombinant WFA modifier without the amino acids between C-terminal side to 13 to $15^{th}$ amino acids, it may be the recombinant WFA modifier forming the monomer that exhibits the LDN sugar-chain specificity that is the same as C272 rWFA.

In the present invention, the recombinant WFA without C-terminal amino acid sequence may be also called a C-terminal side deleted recombinant WFA modifier, "rWFA delta".

"The rWFA delta" may be expressed as follows.

A polypeptide having any one of amino acid sequence represented by the following (1) or (2):

(1) the amino acid sequence, in which any one of the amino acids from C-terminal side thereof to 13 to $15^{th}$ amino acids in the amino acid sequence represented by SEQ ID NO: 2 is deleted; and (2) the amino acid sequence, in which one or several amino acids in the amino acid sequence represented by (1) is/are deleted, substituted, inserted, or added, the polypeptide having LDN-specific sugar-chain recognition ability.

"The rWFA delta" gene may be the base sequence encoding the amino acid sequence represented by the above (1) or (2), but the base sequence may be expressed by any one of the base sequences represented by the following (3) to (6).

(3) the base sequence, in which the base sequence corresponding to any one of amino acid from 3' terminal side to C terminus to 13 to $15^{th}$ amino acids in the base sequence represented by SEQ ID NO: 1 is deleted, and (4) the base sequence that is hybridized with the complementary sequence of the base sequence represented by the above (3) under a stringent condition.

(3-3) Expression of Recombinant WFA Modifier Gene

When the vector including the recombinant WFA modifier gene (C272rWFA or rWFA delta gene) of the present invention is constructed, in order to easily detect C272rWFA or rWFA delta, the tag for detecting, such as, FLAGtag may be bound at an upstream or downstream side. The LDN-specific sugar-chain recognition ability thereof is not changed by binding this tag.

The host and expression vector for expressing the recombinant WFA modifier (C272A rWFA or rWFA delta) of the present invention are the same as the recombinant WFA, and the purification method thereof is the same.

4. As for Reducing WFA Monomer in the Present Invention

In the present invention, "the reducing WFA monomer" indicates monomerized WFA by performing the alkylation treatment of the cysteine residue after reducing to the recombinant WFA or natural WFA of the dimer.

At this time, as the reducing method or alkylation method, it is possible to apply the conventional techniques one by one or at the same time. Typically, after performing the reducing treatment using dithiothreitol (DTT), the technique of reacting with an alkylating agent, such as, iodoacetamide may be applied.

Any kinds of reducing WFA monomers specifically recognize only GalNAc terminal sugar chain, because it does not have the sugar-chain recognition ability to Gal terminal sugar chain.

In other words, a method for preparing the WFA monomer lectin that specifically recognizes GalNAc terminal sugar chain according to the present invention may be expressed as follows.

A method of preparing a WFA monomer lectin that specifically recognizes a GalNAc terminal sugar chain, in which a polypeptide dimer having Gal/GalNAc terminal sugar-chain binding activity, encoding the amino acid sequence represented by the following (1) or (2), is incubated under a reducing condition, and then, at the same time, the alkylation treatment of a sulfur-containing functional group is applied.

(1) The amino acid sequence represented by SEQ ID NO: 2, or the amino acid sequence, in which one or several amino acids at the positions other than $272^{nd}$ position in the amino acid sequence is/are deleted, substituted, inserted, or added, and (2) an amino acid sequence, in which any one of the amino acid sequences between N-terminal side and $30^{th}$ amino acid sequence of the amino acid sequences represented by the above (1) is deleted.

The "WFA monomer lectin" that specifically recognizes GalNAc terminal sugar chain is firstly provided by the present invention.

5. Method for Detecting LDN Sugar-Chain Marker and Kit Therefor

Various recombinants WFA provided in the present invention are useful as a lectin for detecting Gal/GalNAc or GalNAc sugar-chain marker, and may be used for the method of detecting LDN sugar-chain marker, which is conventionally used for a natural WFA.

The rWFA that is called a precursor WFA of a natural WFA has the sugar-chain recognition ability that is the same as the natural WFA, and also, can be massively produced as a WFA gene expression product in a character transformed *E coli*. Therefore, the rWFA may be used as the substitute of the natural WFA for detecting the conventional Gal/GalNAc terminal sugar chain. The monomer rWFA that is obtained by isolating the relevant rWFA through a gel filtration, and the like specifically recognizes LDN sugar chain.

In addition, according to the present invention, when the WFA monomer lectin that specifically recognizes GalNAc terminal sugar chain, and especially, C272 modifier WFA that specifically recognizes only LDN sugar chain among the GalNAc terminal sugar chains are used for the method of detecting LDN sugar-chain marker for detecting a normal gastric mucous membrane area, which is performed using the conventional natural WFA such as the monomer rWFA of C-terminal side, it is possible to exhibit higher specificity.

Specifically, it is considered that it is used as a probe for detecting a small cell carcinoma of lung or an endocrine tumor, in which high expression of LDN sugar chain is expected.

DESCRIPTION OF EMBODIMENTS

Hereinafter, the present invention will be described in detail with reference to Examples, but the present invention is not limited to Examples.

In addition, the technical terms used for the present invention have the meanings that are generally understood by a person who is skilled in the prior art, unless otherwise indicated. In addition, the contents disclosed in Patent Literatures or patent application specifications are incorporated into the description of the present specification.

REAGENTS USED FOR EXAMPLES

The purified *wisteria floribunda* lectin (nWFA) was purchased from Vector Lab Inc. (Burlingame, Calif., USA). An anti-FLAG-tag M2-HRP conjugate was purchased from Sigma-Aldrich Co. LLC. (St. Louis, Mo., USA).

(Example 1) Cloning of *Wisteria Floribunda* Lectin Gene (1-1) Preparation of cDNA Library The total RNA of *wisteria floribunda* seed was extracted using the method of Naito, and others (Non Patent Literature 9). About 150 mg of the seeds were broken in a liquefied nitrogen, the broken product of the seed was mixed with an extraction buffer (1 M Tris-HCl pH 9.0/1% SDS) and PCI (phenol:chloroform:isoamyl alcohol of 25:24:1), and then, was suspended until being in the latex state. After performing the centrifuge, PCI was added in the supernatant thereof, was violently stirred, and then, was centrifuged. Since then, the supernatant was collected, 1/10 times volume of 3 M Na-acetate and 3 times volume of ethanol were added to the supernatant, and then, the supernatant thus obtained was cooled at −80° C. to precipitate the nucleic acids thereof. After performing air-drying, the precipitated nucleic acids were dissolved in $H_2O$, and then, 4 M of LiCl was added thereto. After remaining the reactant thus obtained on an ice overnight, the reactant was centrifuged to collect the total RNA as a precipitate. Poly (A) RNA was prepared using NucleoTrap® mRNA (MACHEREY-NAGEL GmbH & Co. KG, Duren, Germany), and was provided for a cDNA synthesis. The cDNA library used for gene cloning was manufactured using Marathon® cRNA Amplification Kit (Clontech, Mountain View, Calif., USA) from mRNA of *wisteria floribunda* seeds prepared as described above.

(1-2) Gene Cloning

The gene encoding *wisteria floribunda* lectin was cloned from the cDNA derived from *wisteria floribunda* seeds. Using the amino acid sequence (Accession: P05046) of soybean agglutinin (SBA) that was leguminosae lectin as Query, the blast search was performed to obtain three kinds of the amino acid sequences of lectin-typed protein in Genbank DB (*Robinia pseudoacacia*, Accession: BAA36414, *Sophora japonica*, Accession: AAB51441, *Cladrastis kentukea*, Accession: AAC49150). The nucleic acid sequences of these three kinds of lectin-typed proteins (*Robinia pseudoacacia*, Accession: AB012633, *Sophora japonica*, Accession: U63011, *Cladrastis kentukea*, Accession: U21940) were aligned, and then, the following two primers for PCR were designed in the well stored area.

```
                                      (SEQ ID NO. 3)
Fwd-1:     5'-CTCTTGCTACTCAACAAGGTGAA-3'

(SEQ ID NO. 4)
Rev-1:     5'-CAACTCTAACCCACTCCGGAAG-3'
```

The PCR reaction (94° C., 1 min, (30 cycles of 94° C., 1 min—60° C., 30 sec—68° C., 1 min), 68° C., 1 min) of cDNA derived from *wisteria floribunda* seeds as a template was performed with KOD-plus-(TOYOBO, Osaka, Japan). As a result, about 650 bp DNA fragment was amplified. The fragment was sub-cloned in pCR-Blunt II-TOPO (Invitrogen, Carlsbad, Calif., USA), and the nucleic acid sequence thereof was determined with 3130×1 Genetic Analyzer (Applied Biosystems, CA). As a result, it was new nucleic acid sequence.

The sequence was a partial sequence, and did not have the N-terminus and C-terminus of open leading frame, and thus, the sequence of the total length was determined with a RACE (Rapid Amplification of cDNA End) method. For 3'-RACE method, the PCR reaction was performed using the above Fwd-1 and the following Adapter primer-1 (Clontech) primers (35 cycles of 94° C. 1 min, 60° C. 30 sec, and 68° C. 1 min),

```
Adapter Primer-1:
                                      (SEQ ID NO. 5)
5'-CCATCCTAATACGACTCACTATAGGGC-3'
```

Since then, with the amplified nucleic acid as a template, the nested PCR was performed using the above Fwd-2 and the following Adapter primer-2 (Clontech) primers.

```
Adapter Primer-2:
                                      (SEQ ID NO. 6)
5'-ACTCACTATAGGGCTCGAGCGGC-3'
```

As a result of determining the sequence of about 700 bp DNA fragment thus obtained, the gene sequence including a stop codon was obtained.

In addition, for the unknown part of 5' sequence, the following Rev-2 and Rev-3 were designed, and a 5'-Race method was performed using the above Adapter primer-1 and Adapter primer-2 to determine the sequence of total length.

```
                                      (SEQ ID NO. 7)
Rev-2:     5'-ACTATAGACTGGTTCGCCGTCC-3'
```

```
Rev-3:     5'-GGGTGAGTTGTAAATGCCCTGA-3'
                                          (SEQ ID NO. 8)
```

(1-3) Analysis of Sequence of Lectin Gene

The new lectin gene that was subjected to the cloning in *wisteria floribunda* seeds was composed of 861 bp ORF, and thus, encoded the proteins composed of 286 amino acids (FIG. 1). The new amino acid sequence had the motif sequence that was stored in leguminosae lectin, and had the homogeny of 62.8% of *Robinia pseudoacacia*, 60.9% of *Cladrastis kentukea*, and 60.6% of *Sophora japonica*, which were used for query, respectively. In addition, it had the homogeny of 58.5% of soybean lectin SBA (*Glycine max*: P05046) and 39.5% of peanut bean lectin PNA (*Arachis hypogaea*: P02872), respectively (FIG. 2). There was one N-bound sugar-chain addition region in the sequence, and thus, it was confirmed that one cystein residue was existed around C-terminus. The total length-amino acid sequence determined was analyzed using a signal sequence prediction program SignalP4.0 (Technical University of Denmark, http://www.cbs.dtu.dk/services/SignalP/Non Patent Literature 11). As a result, it was predicted that the hydrophobic amino acid cluster at N-terminal side was a signal sequence, and the cutting between $30^{th}$ serine and $31^{st}$ lysine was performed.

(Example 2) Expression of Recombinant Lectin (rWFA) in Transformed *E. coli*

(2-1) Transformation of *E. coli* by Lectin Gene

In order to express the *wisteria floribunda* lectin cloned in Example 1 in *E. coli*, amino acids 31 to 286 residues to be predicted as the lectin activity area were incorporated into a downstream of pelB leader of pET20b (Merck4Biosciences, Darmstadt, Germany) that was a periplasm expression vector after adding His Tag and FLAG Tag at the N-terminus thereof.

In addition, the DNA fragment encoding WFA was amplified with the following WFA-HisFL-Fwd and WFA-Rev, and then, was inserted into NcoI-XhoI region of pET20b.

```
WFA-HisFL-Fwd:
                                          (SEQ ID NO. 9)
5'-
ccatggGACATCATCATCATCATCACCTCGACTACAAGGACGACGATGAC
AAGGGCAAGCTTGCGGCCGCGAATTCAAAAGAAACAACTTCCTTTGTC-
3'

WFA-Rev-1:
                                          (SEQ ID NO. 10)
5'-ctcgagTTAGATGGAACCGCGCAGAA-3'
```

The manufactured plasmid for expression was transformed into *E. coli* BL21-CodonPlus (DE3)-RIPL (Agilent Technologies, CA); the expression of transformant was induced by adding 100 mM isopropyl β-D-thiogalactopyranoside (IPTG) in the final concentration according to a manual; and then, the shaking culture was performed for one night at 25° C.

(2-2) Expression and Purification of rWFA in *E. coli*

The extraction of periplasm fraction was performed according to pET System Manual $11^{th}$ edition (Merck4Biosciences). The extraction of soluble protein was performed using BugBuster (Merck4Biosciences). After inducing the expression, the expression of the recombinant protein was confirmed in the periplasm fraction (FIGS. 3A and 3B). In addition, since it was confirmed that it existed in the soluble fraction, and was leaked in a nutrient medium (lanes 5 and 7 in FIG. 3B), the recombinant protein was purified in a FLAG Tag rather than in the nutrient medium that was easily handled. The purification thereof was performed using DDDDK-tagged Protein PURIFICATION GEL (MBL, Nagoya, Japan), and the recombinant protein was eluted with DDDDK elution peptide. Finally, the eluted protein was concentrated with Amicon Ultra 3K (Merck Millipore, Mass.).

As a result of performing the purification of recombinant lectin by the affinity to a FLAG tag, the recombinant WFA (rWFA) was subjected to a SDS-PAGE under a reducing condition, and then, was obtained by purifying one protein of about 31 KDa that was stained with CBB staining (lane 2 in FIG. 3C).

(Example 3) Confirmation of Identity Between Recombinant WFA (rWFA) and Natural WFA (nWFA) on the Sequence (3-1) Analysis of Amino Acids of Nature-Derived WFA Lectin (nWFA)

The analysis of amino acids of nature-derived *wisteria floribunda* lectin (purchased from Vector Lab) was performed using an amino acid sequencer, Procise492HT (Applied Biosystems, CA) and a mass spectrometer, LTQ Orbitrap Velos ETD (Thermo Fisher Scientific, Waltham, Mass., USA). About 2 μg of lectin protein was treated at 100° C. for 5 minutes in the sample buffer with 2-mercaptoethanol, and then, was subjected to a SDS-PAGE. About 28 KDa band was collected and then reduced-alkylated. The trypsin digestion thereof was performed to decompose the band into the peptide fragments. After concentrating, the analysis of LC/MS was performed using LTQ Orbitrap Velos ETD, and then, the amino acid sequence of constitution peptides was identified.

(3-2) Comparison Result of rWFA and nWFA Sequences

It was confirmed whether or not the estimated amino acid sequence of ORF that was determined by cloning *wisteria floribunda* lectin gene in Example 1 was the same as the WFA lectin available on the market, which was purified from nature. In (3-1), by an amino acid sequencer, the sequence that was the $31^{st}$ lysine of the N-terminal side or less of nWFA (Vector Lab) was identified. In addition, the nWFA was digested with trypsin like (3-1), and the amino acid sequence of constitution peptide was determined by a LC/MS method. As a result, 93% of trypsin digestion peptide obtained from the lectin available on the market was equal to the lectin sequence (except a signal sequence part) that was newly determined (FIG. 8).

In addition, 13-amino acid of C-terminus of WFA-ORF amino sequence determined in Example 1 was not included in the peptide obtained from a nature-derived lectin, and it was considered that there was the possibility of processing it during the maturing process of protein.

(3-3) Comparisons of Dimer Formation Abilities and Molecular Weights by SDS-PAGE The recombinant WFA (rWFA) purified in Example 2 (2-2) was observed as a single band of 31 KDa on a SDS-PAGE under a reducing condition (lane 2 in FIG. 3C). Meanwhile, the natural WFA (nWFA) available on the market was confirmed as a single band of about 28 KDa that was smaller than that of the recombinant WFA (lane 1 in FIG. 3C). As a result of performing a SDS-PAGE under a non-reducing condition except 2-mercaptoethanol, it was suggested that nWFA was detected as a single band of about 60 KDa, thereby forming a dimer with the S—S bond (lane 4 in FIG. 3C). Meanwhile, the rWFA could be detected at both of dimer molecular weight and monomer molecular weight under a non-reducing condition (lane 5 in FIG. 3C).

(Example 4) Production of nWFA Monomer by Reducing Nature-Derived WFA (4-1) Confirmation of Sugar Chain Including Fucose, which was Included in Nature-Derived WFA It was reported that the natural WFA (nWFA) has a sugar chain including fucose, and thus, the lectin blotting was performed using Aleuria Aurantia Lectin (AAL) recognizing fucose. As a result, it was confirmed that the nWFA was a glycoprotein including a sugar chain that reacted to AAL (FIGS. 5A and 5B).

(4-2) Production of nWFA Monomer by nWFA Reduction

The reduction of nature-derived WFA was performed using dithiothreitol (DTT). 10 µL of 1 M DTT was added to 1 mL of 1 mg/mL (100 mM Tris, pH 8.5) nWFA, and then, the reduction reaction was performed at room temperature for 4 hours. Subsequently, 25 µL of 1 M iodoacetamide was added, and then, the alkylation reaction was performed at dark room temperature for 30 minutes. As a result, the nWFA was reduced, and then, cysteine that contributed to the formation of dimer was alkylated to be S-carboxy amide methyl cysteine, and the nWFA was to be a monomer. After the reaction, the extra reagents were removed through ultrafiltration (Amicon 3K, Millipore).

(Example 5) Production of Modifier Lectin C272A (5-1) Expression of Modifier Lectin C272A by *E. coli*

In Example 3 (3-3), since the nWFA was a single band of 28 KDa in the state of non-reduction and a single band of 60 KDa in the state of reduction, it was considered that the nWFA formed a dimer. However, the rWFA was a single band of 31 KDa in the state of reduction, but under the non-reducing condition, the bands were detected at both of the molecular weight of dimer and molecular weight of monomer (FIG. 3C).

In order to verify whether the cysteine residue was involved in forming a dimer, the modifier (C272A), in which only cysteine at $272^{nd}$ position in the rWFA amino acid sequence was substituted by alanine was manufactured, and then, was expressed in *E. coli*.

The modifier lectin C272A was manufactured using PCR with the primers of C272A-Fwd and C272A-Rev.

C272A-Fwd:
(SEQ ID NO. 11)
5'-AGCAGTGATGATGCCAACAACTTGCAT-3'

C272A-Rev:
(SEQ ID NO. 12)
5'-ATGCAAGTTGTTGGCATCATCACTGCT-3'

The FLAG-Tag WFA was manufactured by inserting the fragments amplified using the following N-FLAG and C-FLAG PCR primers, respectively, into EcoRI-XhoI region of pET20b.

N-FLAG:

WFA-FLAG-Fwd:
(SEQ ID NO. 13)
5'-gaattcAGACTACAAGGACGACGATGACAAGAAAGAAACAACTTCCTTTGT-3'

WFA-Rev-2:
(SEQ ID NO. 14)
5'-ggcctcgagTTAGTTGCAATCATCACTGCTAGGATCT-3',

C-FLAG:

WFA-Fwd-1:
(SEQ ID NO. 15)
5'-ggaattcaAAAGAAACAACTTCCTTTGT-3'

WFA-FLAG-Rev:
(SEQ ID NO. 16)
5'-ctcgagTTACTTGTCATCGTCGTCCTTGTAGTCGTTGGCATCATCACTGCTAGGATCT-3'

(5-2) Examination of Dimer Formation Ability by SDS-PAGE

For C272A purified with a FLAG tag, the band of 28 KDa, a monomer size was confirmed on a SDS-PAGE under both of the reducing and non-reducing conditions (lanes 3 and 6 in FIG. 3C). Since the modifier of cysteine did not form a dimer, it was clear that the S—S bond through cysteine was essential for forming a dimer.

(Example 6) Analysis of Sugar-Chain Binding Activity of Recombinant Lectin (rWFA)

(6-1) Measurement of Sugar-Chain Binding Activity

The sugar-chain binding activity of recombinant lectin was analyzed using a complex sugar micro array developed by The National Institute of Advanced Industrial Science and Technology (AIST) (Non Patent Literature 10). The lysine residue of recombinant lectin was labeled with Cy3 (GE Healthcare, Buckinghamshire, UK), and then, was provided to the micro array. The Cy3 signal was measured using Glycostation Reader 1200 (GP BioSciences, Yokohama, Japan).

(6-2) Sugar-Chain Recognition Activity of rWFA

Whether or not the rWFA manufactured in *E. coli* has sugar-chain recognition activity was analyzed using a sugar chain glycoprotein array. The nWFA and rWFA that were labeled with Cy3 were provided to a glycoprotein array. As a result, the nWFA and rWFA exhibited very similar sugar-chain recognition specificity (FIG. 4). One that exhibited strongest signal to both of them was Asialo-BSM (bovine submaxillary mucin). In addition, as expected above, it exhibited the affinity even to the GalNAc terminal sugar chain (A-di, βGalNAc, di-GalNAcβ, LDN, GA2, Tn, Forssman). Furthermore, it exhibited the affinities to asialo-AGP, asialo-TF, asialo-TG, asialo-FET, or the like. From these results, it was clear that the rWFA expressed in *E. coli* had the sugar-chain recognition activity that was the same as the natural WFA.

(6-3) Deletion of C-Terminal 13-Amino Acid, and Effect of $272^{nd}$ Cys Residue on Sugar-Chain Recognition Activity Subsequently, in order to investigate the effect of C-terminal 13-amino acid, the rWFA without 13-amino acid was manufactured, and then, the sugar-chain recognition activity thereof was investigated (FIGS. 5A and 5B). Three kinds of modifiers, such as, the modifier prepared by deleting 13-amino acid and also adding a FLAG-tag to N-terminus (rWFA N-FLAG), the modifier prepared by modifying Cys 272 with Ala in the same design (C272A N-FLAG), and the modifier that was modified, in which the position of FLAG tag (C272A C-FLAG) was changed into C-terminus, were expressed in E. coli (FIG. 5A).

As a result of subjecting the purified recombinant lectin on a SDS-PAGE, the rWFAs N-FLAG without 13-amino acid at C-terminus did not mostly form a dimer, and were electrophoresed on the molecular weight of monomer even under the 2ME-non-reducing condition (lane 6 in FIG. 5B).

In addition, as predicted, it was confirmed that the modified C272A N-FLAG was a monomer, and also, the C272A C-FLAG with the tag at C-terminus was expressed on the monomer (lanes 7 and 8 in FIG. 5B).

Three kinds of purified monomer recombinant lectins were labeled with Cy3, and then, the sugar-chain binding activities thereof were verified with a sugar-chain protein array. As a result, all three kinds of them did not mostly have the sugar-chain recognition activity that was confirmed in nWFA, but only had the binding activity to LDN (GalNAcβ1,4GlcNAc) and asialo-BSM. Here, as compared with the LDN binding activity, the degree of the binding activity to asialo-BSM was insignificant, and thus, the relevant binding activity might be expressed as "LDN-specific binding activity". In addition, the modified C272A WFA having 13-amino acid at C-terminus (lanes 3 and 6 in FIG. 3C) had the same binding activities to LDN and Asialo-BSM, that is, "LDN-specific binding activity" (data is not shown).

Figure 6:
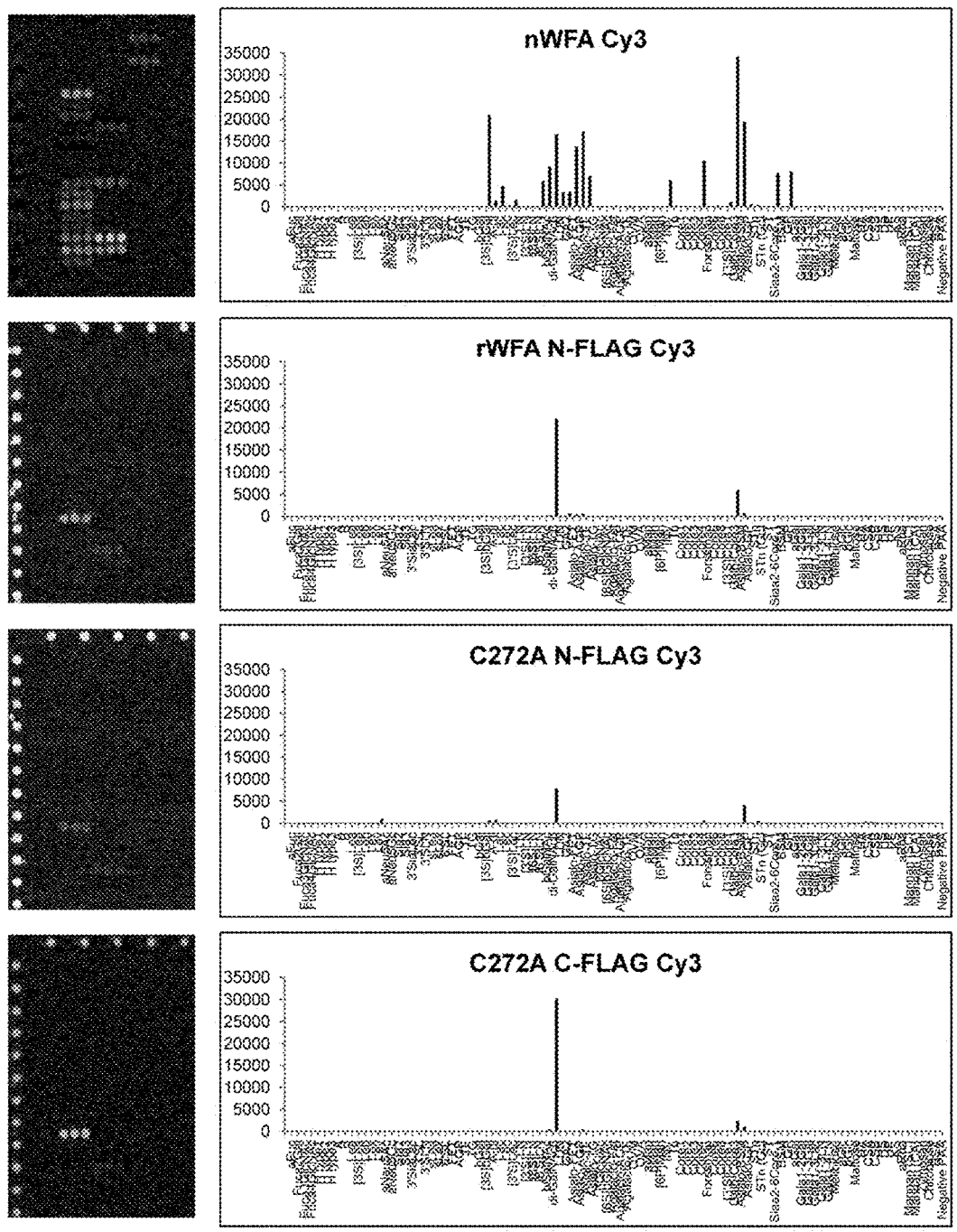
FIG. 6 illustrates the result of a GP array for interpreting sugar-chain binding specificity. All of the monomers rWFA that were newly manufactured with *E. coli* were the lectins that specifically recognize LDN sugar chain.
Figure 9:
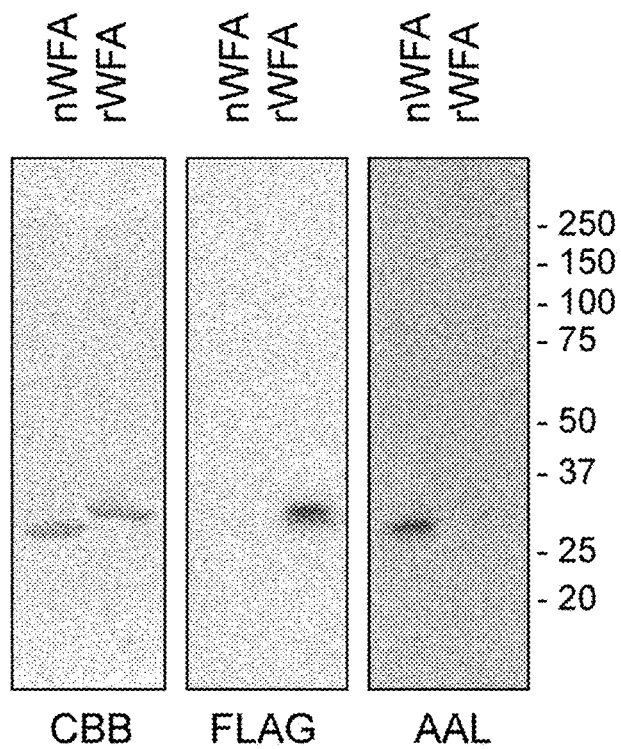
FIG. 9 illustrates staining by various lectins to a natural WFA and rWFA. From the result of lectin blotting using Aleuria *Aurantia* Lectin (AAL) recognizing fucose, it was confirmed that nWFA was a glycoprotein including the sugar chain that reacts the AAL.
Figure 10:
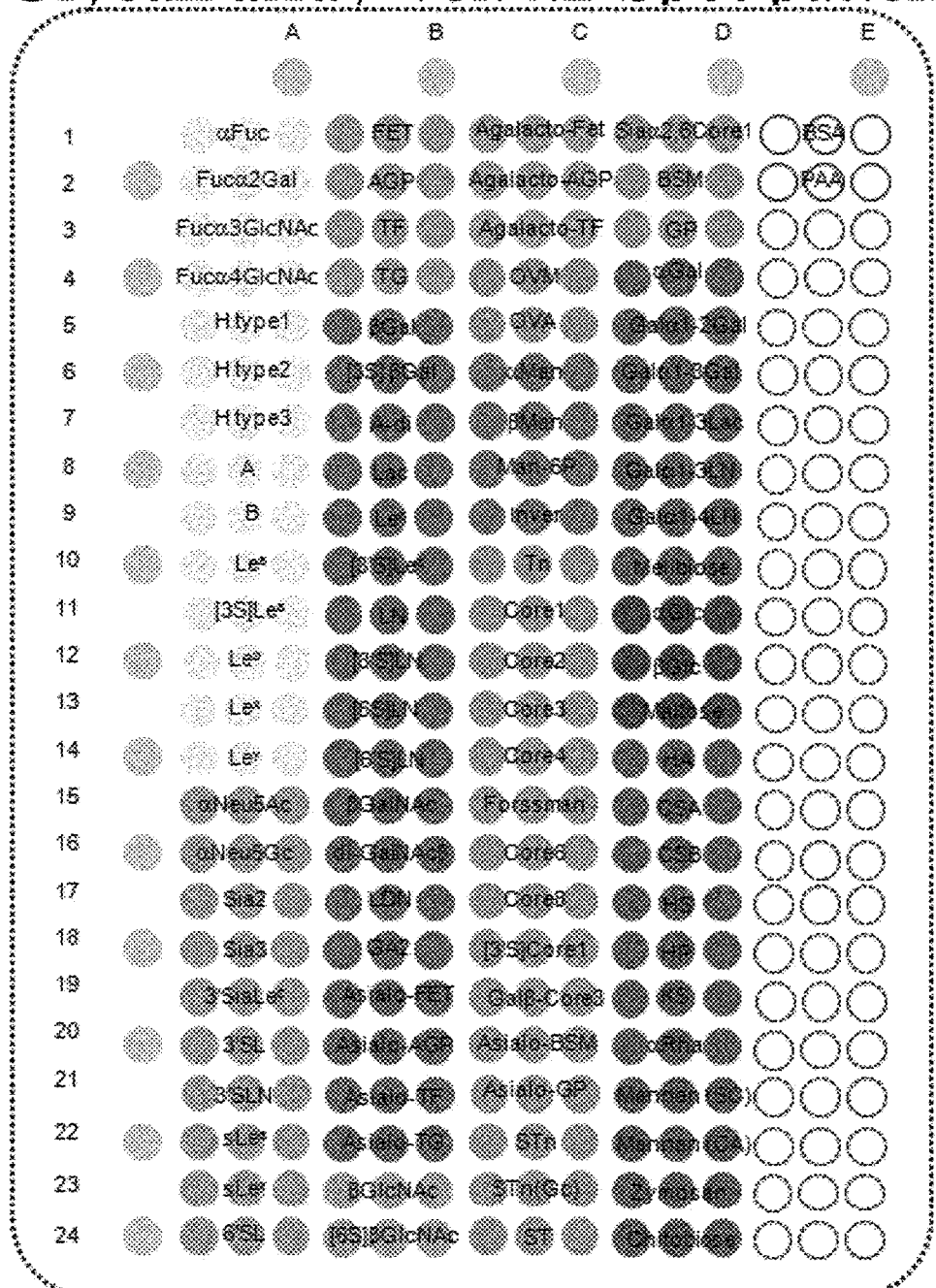
FIG. 10 illustrates the examples of a glycan array.

(6-4) Dimer Formation Ability and Effect on Sugar-Chain Binding Specificity by the Existence of C-Terminal 13-Amino Acid The rWFA, in which the C-terminal 13-amino acid to be predicted to be processed was deleted and a FLAG tag was added to N-terminus or C-terminus, was expressed. As a result, one without 13-amino acid did not mostly form a dimer. The dimer was not detected by a CBB staining, but was only detected by the western blotting of anti-FLAG antibody. The C272A did not form a dimer like Example 5 (FIGS. 3A to 3C). The sugar-chain binding specificity was examined using the purified rWFA (FIG. 6).

(6-5) Explanation of Cause, in which Monomer Recombinant Only Recognizes LDN and Asialo-BSM The rWFA that recognized only LDN and asialo-BSM was a monomer lectin. Therefore, in order to verify whether the difference between the sugar-chain binding activities of nWFA and rWFA occurs by the monomerization or the recombinant expression, the sugar-chain recognition activity of the nWFA monomer having the cysteine residue alkylated after being reduced, which was prepared in Example 4, was reviewed (FIG. 7A).

As a result of analyzing it with a glycoprotein array, the reduced WFA (nWFA-RCA) exhibited the sugar-chain recognition, which was different from nWFA and rWFA. The nWFA-RCA had the significantly decreased or deleted binding activities to Lac, Lec, LN, Asialo-FET, Asialo-AGP, Asialo-TF, Asialo-TG, Tn, Asialo-GP, BSM, and αGal, but the binding activity thereof to the sugar chain having Gal-NAc at the non-reducing terminus, such as A-di, bGalNAc, di-GalNAcβ, LDN, GA2, Forssman, and Asialo-BSM, has changed little (FIG. 7B).

From these results, it was confirmed that the nWFA in a monomer could specifically bind to the sugar chain of GalNAc terminus. In other words, it was confirmed that the dimerized natural WFA could bind to the sugar chain of Gal terminus as well as the sugar chain of GalNAc terminus.

(Example 7) Production of C272A Modified Lectin in Human Culture Cells

The nucleic acid encoding WFA having C272A mutation disclosed in Example (5-1) was introduced into the human culture cells (HEK293T cell line) for reviewing the production of modified lectin in a host other than E. coli. In detail, the gene encoding C272A modified rWFA was inserted into a pFLAG-CMV3 expression vector (Sigma), and then, was transfected into HEK293T cells.

After the gene was introduced into the cells, the cells were cultured in a DMEM medium including 10% bovine serum for 48 hours, and then, the modified lectin was purified from the culture supernatant thereof using an anti-FLAG antibody column (Sigma). As a result, the modified lectin was detected as a single band around about 35 KDa, but there was not observed the increase in molecular weight by the sugar chain (FIG. 12A). It was labeled with Cy3, and was provided to a glycoprotein array. As a result, the binding specificity (LDN and asialo-BSM) like the modified lectin manufactured in E. coli was confirmed (FIG. 12B).

(Example 8) Production of C272A, N146Q Modified Lectin in Human Culture Cells

In this Example, the gene encoding C272A, N146Q modified rWFA of C272A modified lectin that did not give a sugar chain even though it was a eukaryotic cell, in which $146^{th}$ asparagine that was only sugar-chain binding region to the C272A modified rWFA was substituted by glutamine (N146Q), was prepared.

The relevant gene encoding C272A, N146Q modified rWFA was inserted into a pFLAG-CMV3 expression vector (Sigma) that was used in Example 7, and then, was gene-introduced into a human culture cell (HEK293T cell line).

The transformed cells were cultured in the same method as Example 7 to perform the expression induction, and then, the culture supernatant thereof was collected. Using the same purification method as Example 7, the purified C272A, N146Q modified lectin was obtained.

Figure 13:
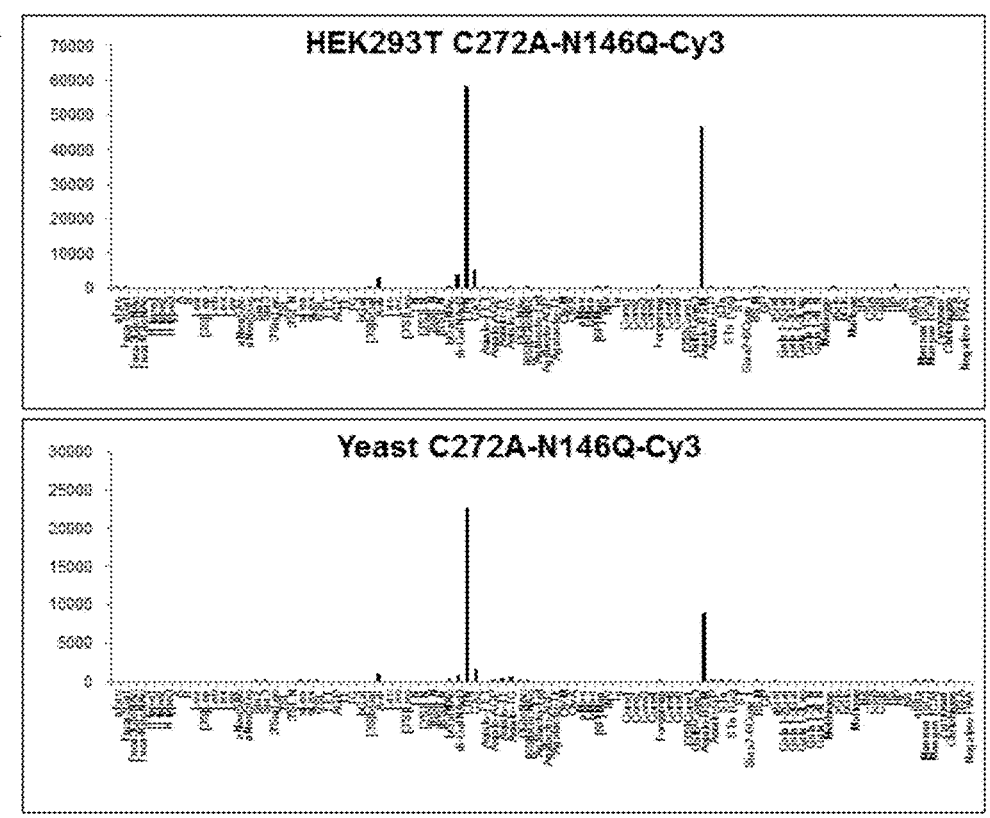
FIGS. 13A and 13B illustrate the purified C272A, N146Q modified rWFA (without N-glycan) produced by mammalian cells and transformed yeasts.

The modified lectin purified from the culture supernatant was detected as a single band of about 33 KDa (Left side in FIG. 13A). It was labeled with Cy3, and then, was provided to a glycoprotein array. As a result, it was confirmed that the binding specificity (LDN and asialo-BSM) like the modified lectin produced in E. coli was exhibited (Upper side in FIG. 13B).

The C272A modified rWFA that was expressed in E. coli, in which the sugar chain could not be added, had LDN-binding activity, and thus, even though it could be sufficiently expected that the addition of sugar chain did not affect the sugar-chain recognition ability, this point became clear from the above result.

(Example 9) Production of C272A, N146Q Modified Lectin in Yeast

As for a yeast (methanol-assimilating yeast Ogataea minuta TK10-1-2 cell line), the gene encoding the C272A, N146Q modified rWFA disclosed in Example 8 was inserted into a pOMEA1-10H3F expression vector having His and FLAG tag to transform O.minutaTK10-1-2 cell line.

The transformed yeast was cultured in 200 ml of YPD medium (2% Peptone, 1% Yeast Extract, and 2% glucose) at 30° C. for 2 days. After removing the culture supernatant by centrifuge, 200 ml of BMMY medium (2% Peptone, 1% Yeast Extract, 1.34% Yeast Nitrogen Base w/o amino acids, 1% MeOH, and 100 mM potassium phosphate buffer (pH6.0)) was added thereto, and then, was re-suspended. Since then, it was further cultured at 30° C. for 2 days, and then, the expression of Endo-Om was performed. After collecting the culture supernatant, the dialysis thereof was performed in TBS buffer (1.24 g of tris(hydroxymethyl) aminomethane, 6.27 g of tris(hydroxymethyl)aminomethane hydrochloride, and 8.77 g/L of sodium chloride). After performing the dialysis, the lectin solution was provided in a HisTrap HP column (GE Healthcare), and then, was washed with a TBS buffer including 50 mM imidazole. Since then, the gradient elution was performed with a TBS buffer including 500 mM imidazole to elute proteins. The fraction including Endo-Om eluted from the column was ultrafiltration-concentrated with Amicon Ultra (10,000 MWCO, Millipore), and also, was substituted with the TBS buffer to be the purified C272A, N146Q modified lectin.

The modified lectin purified from the yeast culture supernatant could be detected as a single band of about 34 KDa (Right side in FIG. 12A). It was labeled with Cy3, and then, was provided to a glycoprotein array. As a result, it was confirmed that the binding specificity (LDN and asialo-BSM) like the modified lectin prepared in *E. coli* and culture cells was exhibited (Bottom side in FIG. 12B).

[Sequence-Free Text]

SEQ ID NO: 1: *wisteria floribunda* lectin (g)
SEQ ID NO: 2: *wisteria floribunda* lectin (a)
SEQ ID NO: 3: Fwd-1
SEQ ID NO: 4: Rev-1
SEQ ID NO: 5: Adapter Primer-1
SEQ ID NO: 6: Adapter Primer-2
SEQ ID NO: 7: Rev-2
SEQ ID NO: 8: Rev-3
SEQ ID NO: 9: WFA-HisFL-Fwd
SEQ ID NO: 10: WFA-Rev-1
SEQ ID NO: 11: C272A-Fwd
SEQ ID NO: 12: C272A-Rev
SEQ ID NO: 13: WFA-FLAG-Fwd (N-FLAG)
SEQ ID NO: 14: WFA-Rev-2 (N-FLAG)
SEQ ID NO: 15: WFA-Fwd-1 (C-FLAG)
SEQ ID NO: 16: WFA-FLAG-Rev (C-FLAG)

The invention claimed is:

1. A *Wisteria floribunda* monomeric lectin polypeptide comprising any one of the amino acid sequences selected from the group consisting of:
   (1) the amino acid sequence represented by SEQ ID NO: 2 except that Cys272 is substituted with an amino acid other than Cys;
   (2) the amino acid sequence defined in (1) above, except that one to 20 amino acids at positions other than Cys272 is/are deleted, substituted, inserted, or added;
   (3) the amino acid sequence identical to the amino acid sequence represented by SEQ ID NO: 2 except that 13 to 15 amino acids are deleted from the C-terminus of SEQ ID NO: 2; and
   (4) the amino acid sequence defined in (1) to (3) above, further having an N-terminus deletion of one to 30 amino acids,
   wherein the polypeptide is capable of specifically binding to LDN sugar chain.

2. A reagent composition for detecting a LDN sugar chain marker, wherein the reagent comprises the polypeptide of claim 1.

3. A cDNA molecule encoding a *Wisteria floribunda* monomeric lectin polypeptide comprising any one of the amino acid sequences selected from the group consisting of:
   (1) the amino acid sequence represented by SEQ ID NO: 2 except that Cys272 is substituted with an amino acid other than Cys;
   (2) the amino acid sequence defined in (1) above, except that one to 20 amino acids at positions other than Cys272 position is/are deleted, substituted, inserted, or added;
   (3) the amino acid sequence represented by SEQ ID NO: 2 except that 13 to 15 amino acids are deleted from the C-terminus of SEQ ID NO: 2; and
   (4) the amino acid sequence defined in (1) to (3) above, further having an N-terminus deletion of one to 30 amino acids,
   wherein the polypeptide is capable of specifically binding to LDN sugar chain.

4. An expression vector comprising the cDNA of claim 3.

5. A transformed cell transformed by using the cDNA of claim 3.

6. A method for preparing a recombinant polypeptide having LDN sugar-chain-specific binding activity, the method comprising the steps of:
   culturing the transformed cell of claim 5; and
   collecting an expression product from a culture product obtained by culturing the transformed cell of claim 5.

7. A method for diagnosing development of a disease defined by high expression of LDN sugar chain in a subject, the method comprising the step of detecting a LDN sugar chain marker by binding the reagent composition of claim 2 to cells having high expression of LDN sugar chain in said subject and diagnosing the development of the disease defined by high expression of LDN sugar chain in said subject.

8. The method of claim 7, wherein the disease defined by high expression of LDN sugar chain is an endocrine tumor or a lung small cell carcinoma.

* * * * *